(12) United States Patent
Sonnenschein et al.

(10) Patent No.: US 8,678,994 B2
(45) Date of Patent: Mar. 25, 2014

(54) DEVICES AND METHODS FOR TREATING MORBID OBESITY

(75) Inventors: Elazar Sonnenschein, Beer Sheva (IL); Amir Govrin, Tel Aviv (IL); Yoav Avidor, Tel Aviv (IL); Yuval Elovici, Moshav Arugot (IL); Minelu Sonnenschein, Meitar (IL)

(73) Assignee: Medigus Ltd., Omer (IL)

( * ) Notice: Subject to any disclaimer, the term of this patent is extended or adjusted under 35 U.S.C. 154(b) by 493 days.

(21) Appl. No.: 12/713,320

(22) Filed: Feb. 26, 2010

(65) Prior Publication Data

US 2010/0168768 A1 Jul. 1, 2010

Related U.S. Application Data

(62) Division of application No. 11/825,694, filed on Jul. 9, 2007, now Pat. No. 7,841,503.

(30) Foreign Application Priority Data

Jul. 16, 2006 (IL) .......................................... 176889

(51) Int. Cl.
*A61F 2/00* (2006.01)
*A61F 13/00* (2006.01)
*A61B 1/00* (2006.01)

(52) U.S. Cl.
USPC ............. 600/37; 600/101; 606/139; 606/157; 606/101

(58) Field of Classification Search
USPC .................... 600/37, 101; 606/139, 157, 101; 128/898
See application file for complete search history.

(56) References Cited

U.S. PATENT DOCUMENTS

| 6,572,629 B2 | 6/2003 | Kalloo et al. |
| 2001/0049497 A1 | 12/2001 | Kalloo et al. |
| 2003/0163029 A1* | 8/2003 | Sonnenschein et al. ...... 600/160 |
| 2004/0044354 A1* | 3/2004 | Gannoe et al. ................ 606/153 |
| 2005/0143766 A1* | 6/2005 | Bachmann et al. ........... 606/158 |

FOREIGN PATENT DOCUMENTS

| WO | WO 01/67964 | 9/2001 |
| WO | WO 02/24058 | 3/2002 |
| WO | WO 02/39909 | 5/2002 |
| WO | WO 02/068988 | 9/2002 |
| WO | WO 2005/002210 | 1/2005 |
| WO | WO 2005/115221 | 12/2005 |
| WO | WO 2005/115255 | 12/2005 |
| WO | WO 2005/120329 | 12/2005 |
| WO | WO 2006/033109 | 3/2006 |

OTHER PUBLICATIONS

Lee WJ, Yu PJ, Wang W, Chen TC, Wei PL, Huang MT. Laparoscopic Roux-en-Y versus mini-gastric bypass for the treatment of morbid obesity: a prospective randomized controlled clinical trial. Ann Surg. 2005;242(1):20.*

(Continued)

*Primary Examiner* — Christine Matthews
*Assistant Examiner* — Sunita Reddy
(74) *Attorney, Agent, or Firm* — Roach Brown McCarthy & Gruber P.C.; Kevin D. McCarthy

(57) ABSTRACT

A surgical method of treating morbid obesity via bariatric procedures, carried out endoluminally and transluminally using endoscopic devices that are introduced through natural body openings without the necessity of creating any incisions in the abdominal wall.

10 Claims, 41 Drawing Sheets

(56) References Cited

OTHER PUBLICATIONS

U.S. Appl. No. 11/446,740, filed Dec. 6, 2007, Medigus Ltd.
Health Implications of Obesity. National Institutes of Health (NIH) Consensus Statement Online Feb. 11-13, 1985; 5(9)1-7....
Friedman JM, Leptin and the Regulation of Body Weight in Mammals. Nature, 1998; 395:763-770....
Ramsey-Stewart G, Martin L: Jaw wiring in the treatment of morbid obesity. Aust N Z J Surg Apr. 1985; 55(2):163-7....
Buchwald, Avidor, Braunwald, et al. JAMA, Oct. 2004....
Chritou N, et al. Ann Surg, Aug. 2004....

* cited by examiner

  
Fig. 16A          Fig. 16B          Fig. 16C
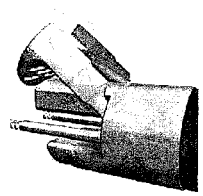  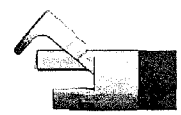
Fig. 16D          Fig. 16E          Fig. 16F

DEVICES AND METHODS FOR TREATING MORBID OBESITY

CROSS-REFERENCES TO RELATED APPLICATION

This application claims priority as a divisional application of U.S. patent application Ser. No. 11/825,694, filed on Jul. 9, 2007 now U.S. Pat. No. 7,841,503; which claims priority to Israeli patent application serial number 176889, filed on Jul. 16, 2006.

FIELD OF THE INVENTION

The invention is related to the field of medical devices. More specifically the invention relates to endoscopic devices for treating morbid obesity and for methods of using these devices.

BACKGROUND OF THE INVENTION

There are several methods for assessing and describing the presence of excess weight. However, most authorities now define excess weight in terms of the Body Mass Index (BMI). The BMI is calculated by dividing the weight in kilograms by the square of the height in meters. For example, a 1.75 m tall man who weighs 85 kg has a BMI of $85/(1.75)^2$ or $85/3.0625=28$. A person with a height of 1.6 m having the same weight will have a BMI of 33. Individuals are considered to suffer from morbid obesity if their BMI is $\geq 40.0$ or if their BMI has a value of 35.0-39.9 and they suffer from obesity related medical problems.

In earlier times, being obese was considered a sign of good health. However, it is now clear that obesity is associated with a number of serious conditions, and that it is a major health risk, whose prevalence is rising. Overweight and obesity are known risk factors for: diabetes, heart disease, stroke, hypertension, gallbladder disease, osteoarthritis, sleep apnea and other breathing problems, and some forms of cancer (uterine, breast, colorectal, kidney, and gallbladder). In addition obesity is associated with: high blood cholesterol, complications of pregnancy, menstrual irregularities, hirsutism, stress urinary incontinence, psychological disorders such as depression, and increased surgical risk.

It is evident then that obesity is a major health problem and is now considered an epidemic in the western world and is beginning to be a serious problem in areas of the world where it has traditionally been virtually unknown. The prevalence of obesity in many western countries is alarmingly high. For example, from data available for 1999, over ten million people suffered from morbid obesity, as defined above, in the United States of America and the deaths of an estimated 300,000 to 600,000 people could be related to obesity.

Despite these facts, many people regard obesity as being due to lack of will power and that it is solely due to bad eating habits and lack of exercise. The consensus amongst health care professionals today however is that obesity is a disease in its own right. As summarized by the National Institutes of Health in 1985 [Health Implications of Obesity. NIH Consensus Statement Online 1985 Feb. 11-13; 5(9):1-7];

Formerly, obesity was considered fully explained by the single adverse behavior of inappropriate eating in the setting of attractive foods. The study of animal models of obesity, biochemical alterations in man and experimental animals, and the complex interactions of psychosocial and cultural factors that create susceptibility to human obesity indicate that this disease in man is complex and deeply rooted in biologic systems. Thus, it is almost certain that obesity has multiple causes and that there are different types of obesity.

Physical inactivity and nutrition are only two of many causal factors of obesity, as the disease is currently understood. Other factors are genetic predisposition, environmental factors (social and cultural), physiologic and metabolic factors, behavioral, and psychological conditions. There is no question that physical activity and nutrition are factors in the development, management and prevention of obesity. However, research is progressively increasing our understanding of the critical roles played by genetic factors and psychological factors. "The belief that obesity is largely the result of a lack of willpower, though widely held, is unsatisfactory. Studies of twins, analyses of familial aggregation, adoption studies and animal models of obesity all indicate that obesity is the result of a high percentage of genetic as well as of environmental factors." [Friedman J M, Leptin and the Regulation of Body Weight in Mammals. Nature, 1998; 395:763-770].

To summarize present day thinking, obesity is a disease in its own right, and that treatment strategies should (and are) be developed to combat it.

Current treatment options for obesity include both non-surgical and surgical methods. Non-surgical approaches to treatment of clinically severe obesity include various combinations of low- or very low-calorie diets, behavioral modification, exercise, and pharmacologic agents.

The obvious solution to obesity is to eat less. It is quite obvious that less food intake will result is weight loss. However, diet in many forms has proven inadequate to control obesity particularly in morbid obesity. Significant weight reduction, for example 20 kg over 12 weeks, can be expected. However, in the absence of successful behavior modification, most patients regain their lost weight within 1 year. Additionally, medical complications of rapid weight loss may occur. These are usually treatable if recognized and their occurrence can be limited by proper medical supervision. Behavioral modification is a therapeutic approach based on the assumption that habitual eating and physical activity behaviors must be relearned to promote long-term weight change. Behavioral treatment also can be combined with a lesser degree of caloric restriction, although evidence of long-term efficacy of this more conservative approach in persons with clinically severe obesity is lacking. Increased physical activity is recommended as a component of weight-loss programs; however, the role of exercise in promoting and sustaining weight loss has never been established. Experience with drug therapy for clinically severe obesity has been disappointing. Although pharmacologic studies with anorexigenic drugs suggest short-term benefit, prolonged and sustained weight loss has not been proved with these agents. The general weight of the evidence that has been obtained in recognized clinical trials is that only in rare cases of a highly disciplined and motivated patient has safe long term weight loss been achieved by non-surgical methods of treatment of morbid obesity.

Various surgical approaches to morbid obesity have been tried over the years. In general, the surgical techniques can be regarded as either malabsorptive or restrictive.

Malabsorptive procedures modify the gastrointestinal tract so that only a small fraction of the food intake is actually digested. Following a malabsorptive procedure, the patient can continue to gorge himself, but the food is not fully digested, and the amount of calories and nutrients absorbed is small.

Restrictive procedures work by limiting food intake. Following a restrictive procedure, the patient's ability to eat is severely restricted. The patient can only eat a limited amount of food. Any attempt to eat more, will result in varying degrees of discomfort. In addition to forcing the patient to eat less, the discomfort conditions the patient to chew his food well, and obtain healthier eating habits, which may outlive the restriction in certain cases.

It is possible to combine restrictive and malabsorptive procedures, and achieve greater weight loss. The leading bariatric procedure in the US right now is Roux en Y Gastric Bypass which combines stomach restriction with malabsorption, which is achieved by bypassing the proximal small intestine.

In general, malabsorptive procedures are usually more technically challenging and result in greater weight loss. The first malabsorptive procedure, called the Jejuno-ileal bypass, was associated with so many late complications that it is now abandoned. The main malabsorptive operations currently performed are the Scopinaro Biliopancreatic Bypass and the Duodenal Switch procedure. In competent hands these are highly successful operations.

The restrictive procedures that are currently being used or have been practiced in the past include:

Jaw wiring is a method for restricting weight by wiring the jaws shut. After jaw wiring, the patients can only take fluids with a straw. This usually results in significant weight loss. However, almost all patients regain their weight soon after the wires are removed. In addition, a high percentage of patients cannot tolerate the wires, and request to have them removed or remove them by themselves [Ramsey-Stewart G, Martin. L: Jaw wiring in the treatment of morbid obesity. Aust N Z J Surg 1985 April; 55(2):163-7].

Because of these limitations, jaw wiring is no longer a commonly offered option to patients. A Medline search for Jaw wiring and obesity showed that no articles on Jaw wiring as a treatment for morbid obesity had been published since 1985. The last paper, published in 1993, showed that using jaw wiring as a prelude to bariatric operation did not influence the long-term weight loss, when compared to controls.

The Intragastric balloon, sometimes known as the gastric bubble, was introduced in the late 1980's as a non-invasive method for treating obesity. There are a number of commercially available balloons, usually made of silicone rubber. They are placed in the stomach by oral endoscopy, and inflated to 400-600 ml. The idea being that the balloon fills the stomach, restricting its volume, and at the same time produces a sensation of satiety. Attractive as it seemed at the time of its introduction, and in spite of a few early clinical trials showing weight loss, a number of randomized controlled trials failed to show its efficacy.

Even in the early clinical trials, the benefit observed disappeared quickly, even if the balloon was maintained inflated. From these results it is evident that the intragastric balloon is not a good solution to the problem of obesity, although it may have a useful role in interim management of selected patients.

Horizontal gastroplasty, developed by Gomez in Ohio in 1979, was the first attempt at a gastric restrictive operation. The early use of stapling devices in obesity surgery involved removal of three staples from the row and firing the stapler across the top part of the stomach. As a result, the two stomach walls are stapled together, except at the point where the three staples were removed, where a small gap remains. The idea being that food, which the patient takes in, is retained in the segment of stomach above the staple line causing the sensation of fullness. The food then empties slowly through the gap (stoma) into the part of the stomach below the staple line where digestion takes place normally.

Early results were very encouraging. They showed that the food in the small pouch indeed produced a sensation of satiety and that the patients lost weight rapidly. Unfortunately, the muscular stomach wall has a tendency to stretch and the stoma enlarges. Sometimes the staple line failed. To combat these problems, other procedures in which the stoma was moved to the side and reinforced were introduced. Because the procedures discussed below had better long-term results, horizontal gastroplasty fell out of favor and is now practically abandoned. However, the results of horizontal gastroplasty are still much better than the results of non-surgical treatment, intra-gastric balloon, or jaw wiring.

Vertical banded gastroplasty (VBG) was introduced by Dr. Edward Mason, Professor of Surgery at the University of Iowa, in 1982 to overcome the shortcomings of horizontal gastroplasty described above. Mason realized that the lesser curvature part of the stomach had the thickest wall and was therefore least likely to stretch; therefore he used a vertical segment of stomach along the lesser curvature for the pouch. Additionally, he was very meticulous in defining the size of the pouch, measuring it at surgery under a standard hydrostatic pressure, and has shown that best results follow the use of a very small pouch, holding only 14 cc saline at the time of surgery. The third modification which he made was to place a polypropylene band (Marlex Mesh) around the lower end of the vertical pouch, which acts as the stoma, to fix the size of the outlet of the pouch preventing it from stretching. This is done by use of a circular stapling instrument to staple the front and back walls of the stomach together, cutting out a circular window to allow the polypropylene band to be placed around the lower end of the pouch. His extensive studies showed that the correct circumference of the band is 5.0 cm. Correctly performed this operation produces good weight loss results. There are few complications associated with Vertical Banded Gastroplasty, because all food taken in is digested normally. Anemia is rare and vitamin B12 deficiency is almost unknown. The patient does have to be very careful to chew food completely to avoid vomiting, and to avoid high calorie liquids such as regular sodas and ice cream. A surgical variant of the VBG is the Silastic Ring Vertical Gastroplasty (SRVG), which is functionally identical to VBG but uses a silastic ring to control the stoma size. These procedures were mostly abandoned due to weight regain caused by gradual opening of the staple line. Surgeons who previously performed VBG or SRVG migrated to the more contemporary and successful RYGB and AGB (see below).

Roux-en-Y Gastric Bypass (RYGB) was also developed by Dr Edward E. Mason, of the University of Iowa. It is mainly a restrictive procedure, but also causes some malabsorption. Its evolution since its introduction in 1967 is quite convoluted, but it is an operation that has endured the test of time. With one series of greater than 500 cases, followed for 14 years, maintaining 50% excess weight loss, RYGB is the gold standard for bariatric operations. The operation involves using a stapler to close off most of the stomach leaving a small pouch at the entrance. The small intestine is separated from the large one and joined to the stomach pouch.

Besides causing significant weight loss, on the order of 70% excess weight loss (% EWL), RYGB brings about resolution of obesity related comorbidities in most patients, including most cases of type 2 diabetes, obstructive sleep apnea, hypertension and hyperlipidemia (Buchwald, Avidor, Braunwald, et al. JAMA, October 2004). Additional studies indicate a significant survival benefit for morbidly obese patient who undergo RYGB as compared with morbidly obese controls who do not undergo surgery (Chritou N, et al. Ann Surg, August 2004).

Staple line failures with ensuing weight regain have been found to occur many years after the procedure. As a result surgeons have responded by use of techniques designed to prevent this including transection of the stomach, in which the staple line is divided and the cut ends oversewn.

The complications of gastric bypass are much less severe than those of Malabsorptive procedures. Most large series studies report complications in two phases, those, which occur shortly after surgery, and those, which take a longer time to develop. The most serious acute complications include leaks at the junction of stomach and small intestine. Complications which develop later include narrowing of the stoma (the junction between stomach pouch and intestine), which results from scar tissue development. This opening is made to be about 10 mm in diameter, therefore a very little scarring will reduce the opening to a degree that affects the patients eating. Wound hernias occur in 5-10% and intestinal obstruction in 2% of patients, an incidence similar to that following any general surgical abdominal procedure. Metabolic complications that occur following RYGBP include anemia and calcium deficit, because essential nutrients for blood production (iron and vitamin B12) depend on the stomach for absorption, and because calcium is best absorbed in the duodenum which is bypassed.

With the advent of laparoscopic surgery, a minimal access surgical solution for morbid obesity was investigated in many centers. Surgeons in the US have developed laparoscopic techniques for performing a RYGB. These techniques are quite successful and currently over 75% of RYGB procedures are done laparoscopically. Complication rate is low and early results compare favorably with open RYBG. However, the technique is challenging, and is associated with a long learning curve of about 100 procedures.

Adjustable Gastric banding (AGB) represents a revival of horizontal gastroplasty in which a silicone band is placed around the stomach. There are two leading adjustable bands on the market today. One was developed jointly in Italy and in Belgium and the other in Sweden. The differences between the two are small. In both, a silicone band, with an inflatable cushion inside is placed around the stomach, and sutured in place. At a later date, the band is inflated to tighten the closure. If the patient gains weight, the band is inflated again. If the patient loses too much weight, the band is deflated. The long-term results of laparoscopic gastric banding are not known, but early results seem to compare well with other purely restrictive procedures such as SRVG or VBG described above.

An endoscopic procedure for reducing capacity has been proposed in U.S. Pat. No. 6,572,629 by Kalloo, et al. In this method a ligating loop is clipped either to the interior of the stomach or around the outside of the stomach and pulled tight and tied in order to effectively reduce the size of the stomach. The loop is attached to the interior walls of the stomach with a flexible endoscope introduced through the esophagus. The loop is attached on the outside of the stomach by creating an opening in the stomach and causing the end of the endoscope to exit the stomach into the peritoneal cavity. Some of the techniques used are described in an earlier patent, U.S. Pat. No. 7,721,742, by the same inventors.

To summarize the current state of the art of surgical options in the treatment of obesity, the ideal bariatric operation is one which is simple, carries few complications, and results in a predictable and sustained weight loss. Such an operation does not exist.

The best long-term results are 80% % EWL at 5 years, for the Biliary pancreatic bypass operation. However these results are achieved using a very complex operation, with a high complication rate in non-expert hands. The various restrictive and hybrid operations yield a two-year EWL of between 50% (AGB) and 65-70% (RYGB). These results are far superior to the results of non surgical treatment. Even the simplest gastric restrictive operation—stapled horizontal gastroplasty—is superior to diet alone. Long-term success rate varies between 30 and 60% versus, 10-15% for the most successful nonoperative schemes.

However, because of the complications of surgery: any of the above procedures is associated with some risk. For this reason the operative approach, using any of the known methods, is limited to the morbidly obese. In these patients the risks are justified, even with the imperfect results of surgery. Patients who are merely obese, and certainly overweight persons, are not candidates for any of these procedures. This mirrors the guidelines established by NIH in 1991 for weight loss surgery.

It is therefore a purpose of the present invention to provide bariatric procedures that overcome the shortcomings of the prior art.

It is another purpose of the present invention to provide bariatric procedures that are carried out endoscopically or laparoscopically.

It is a further purpose of the present invention to provide endoscopic and laparoscopic devices for carrying out bariatric procedures.

Further purposes and advantages of this invention will appear as the description proceeds.

SUMMARY OF THE INVENTION

The invention is a surgical method of treating morbid obesity. The method is carried out endoluminally or transluminally using endoscopic devices that are introduced through natural body openings without the necessity of creating any incisions in the abdominal wall.

A first aspect of the surgical method of the invention comprises positioning an adjustable gastric band around a portion of the stomach. In one embodiment the adjustable gastric band is applied using a transgastric procedure. In another embodiment, carried out entirely within the stomach, the stomach wall is plicated and attached to the external wall of the cardia in at least two locations and the adjustable gastric band is applied within the stomach around the loops created by the plications. In yet another embodiment the stomach wall is plicated and attached to the external wall of the cardia in at least two locations and the adjustable gastric band is applied around the outer wall of the cardia within the loops created by the plications.

A second aspect of the surgical method of the invention comprises performing the first stage of a gastric bypass procedure by bisecting the stomach to form a closed pouch. The stomach can be bisected by introducing the endoscopic devices transorally through the esophagus into the stomach or through the anus and part of the colon into the abdominal cavity.

A third aspect of the surgical method of the invention comprises a method of performing the second stage of performing a Gastric Bypass procedure. The Gastric Bypass procedure can be a mini Gastric Bypass or a complete Roux-en-Y Gastric Bypass.

In a final aspect the invention is endoscopic devices that can be introduced through natural body openings to carry out surgical methods of treating morbid obesity endoluminally or transluminally.

All the above and other characteristics and advantages of the invention will be further understood through the following illustrative and non-limitative description of preferred embodiments thereof, with reference to the appended drawings.

BRIEF DESCRIPTION OF THE DRAWINGS

FIGS. 16A to 16F schematically show different stages in the operation of the front fastening embodiment of the endoscopic stapler used to close a hole in biological tissue;

DETAILED DESCRIPTION OF PREFERRED EMBODIMENTS

Figure 1A:
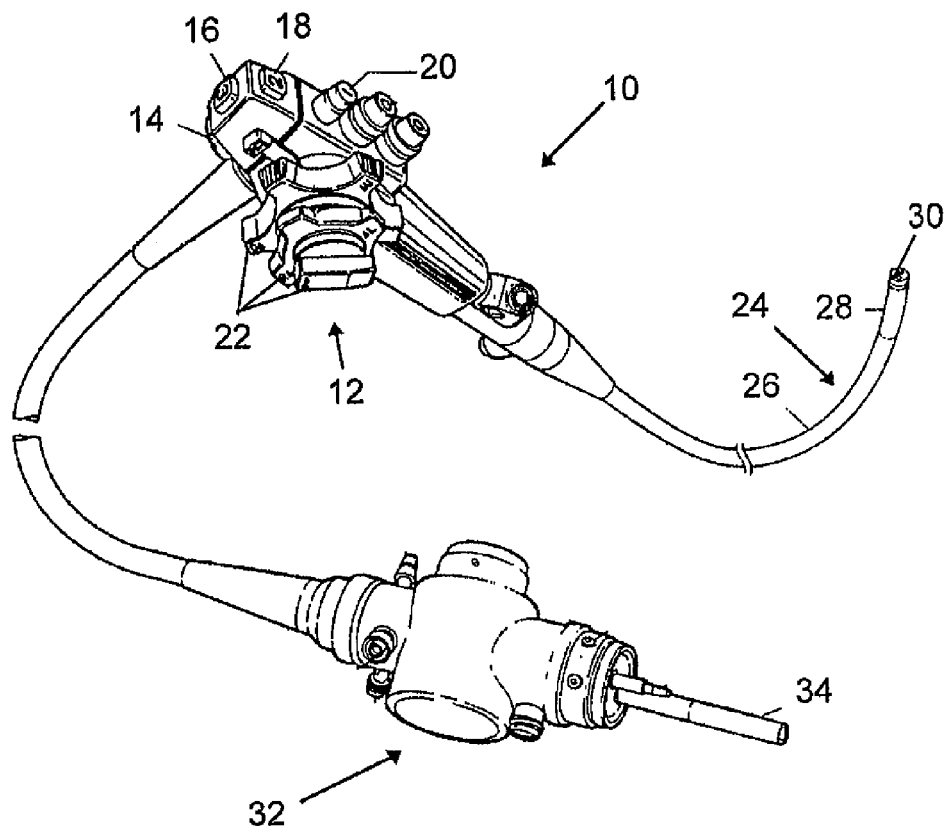
FIGS. 1A and 1B schematically illustrate a conventional endoscope.

Many different types and embodiments of endoscopic apparatus have been developed over a period of several years by the Applicant of the present application. These inventions are described in published International Patent Applications WO01/67964, WO/02/39909, WO02/24058, WO02/068988, WO2005/002210, WO2005/115221, WO2005/115255, WO2005/120329, and WO2006/033109 and in U.S. Pat. No. 7,530,984 all by the same applicant hereof, the descriptions of which, including publications referenced therein, are incorporated herein by reference.

One or more of several different types of endoscopic devices are used to carry out the novel transluminal procedures for treatment of morbid obesity to be described hereinbelow. All of these endoscopic devices comprise at least one video camera and illumination fibers to provide real time visualization of the operating site. Cameras that have been developed for use with endoscopes, including cameras having diameters of less that can be installed on a distal tip of less than 2 mm diameter are described in WO2005/002210 and WO2005/115221. Cameras that are based on CMOS and CCD technology can be manufactured at a cost that is low enough to allow them to be discarded after a single use.

Each of the endoscopic devices is connected to an endoscopy suite such as that described in WO2005/120329 to provide safe supply of light, air, vacuum, water, etc. as required for the particular phase of the procedure for which the specific endoscope is employed.

The several basic types of endoscope that are required are: (a) a GERD type endoscope with stapler; (b) a working channel endoscope, which has no stapler but one or more working channels; (c) baby scope; (d) an endoscope with stapler on distal tip to close holes; (e) an endoscope with one linear stapler on its distal end to simultaneously make two parallel staple lines; and (f) an endoscope with two linear staplers on the distal end to independently make two single staple lines.

A brief description of each of these types of endoscopic devices follows:

(a) GERD Type Endoscope with Stapler

WO01/67964 describes an endoscopic device comprising a surgical stapler attached to its shaft in such a way that bending the articulation section of the endoscope through an angle of 270° brings the anvil of the stapler, located on the distal tip of the endoscope, into correct working position with the cartridge containing the staples and staple firing mechanism, located on the insertion section at the proximal end of the articulation section. The endoscope-stapler unit was initially designed for performing fundoplication procedures as a treatment for GERD. Experienced persons will realize however, that the basic device itself and in particular the improvements to many of its components and subsystems described in the other above referenced applications are not limited to any particular application and can be either used as described or modified mutatis mutandis by skilled persons for many applications in medicine and industry.

Figure 1B:
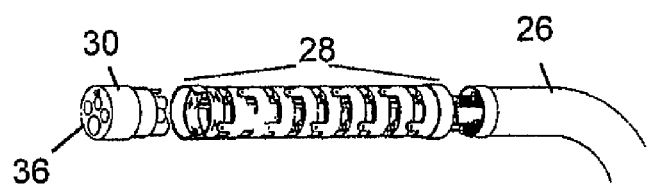

A conventional endoscope is illustrated in FIGS. 1A and 1B. Briefly the endoscope illustrated in FIG. 1A and generally indicated at 10, is provided with a control section 12 (referred to as the "handle", "control handle", "operating handle") provided with suction valves, operating switches, articulation lock, etc., switches 14-20 being marked for illustrative purposes. Control wheels 22 are used for implementing the bending of the articulation section, locking the articulation section, activating accessories such as a stapler, etc. The endoscope 10 also comprises a connector section 32, which is used to connect air and water lines, light guides, etc. to the endoscope.

The light guide is indicated at 34, for illustration purposes. The insertion tube 24 consists of three separate sections: a flexible portion 26, an articulation section 28 and a distal tip section 30. These latter three sections are shown in greater detail in FIG. 1B, in which is also shown the distal face 36.

The handle 12 of the endoscope includes connections, control knobs, and mechanisms for carrying out the functions of the endoscope. These functions include conventional operations, e.g. articulation, staple firing, and specialized operations, e.g. staple cartridge indexing, advancement of the screws that lock the anvil to the cartridge, ultrasonic positioning that are unique to the endoscopes described in the above referenced patent applications, which are suitable for carrying out the procedure of the present invention. The handle is connected by means of the universal multi-connector, vacuum and water lines, etc. to an endoscopy suite such as that described in WO2005/120329.

Figure 2:
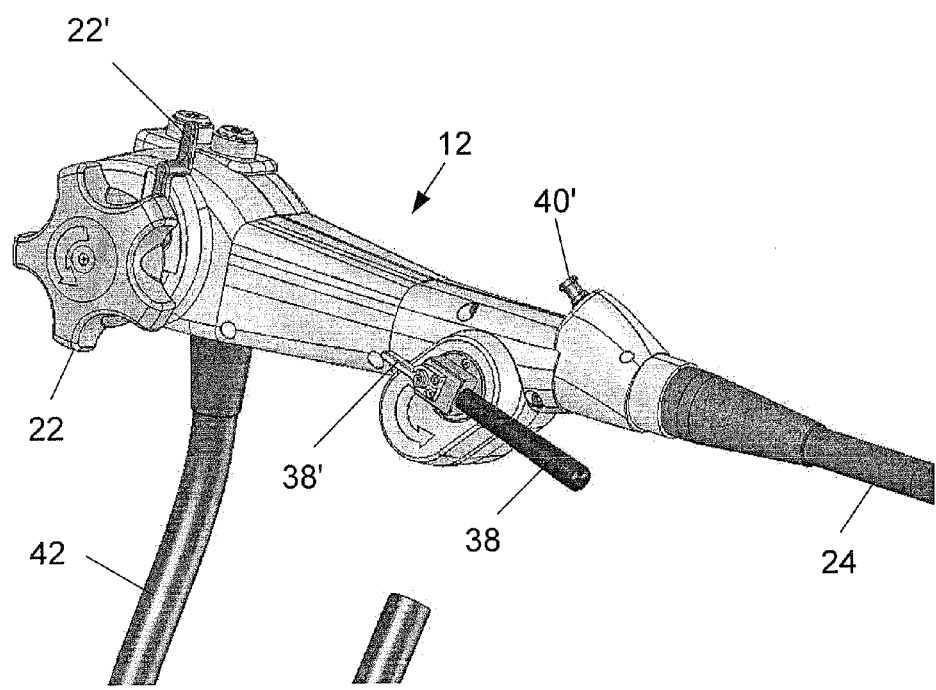
FIG. 2 shows the handle of the prior art GERD endoscope.

In FIG. 2 is shown an illustrative handle 12 that comprises all of the control elements needed to perform the method of the invention described herein. In this figure are seen: the control knob 22 for bending of the articulation section with associated lever 22' which activates a ratchet mechanism for fine control of the bending and also locking the articulation section; the staple firing lever 38 and associated locking lever 38', which prevents accidental firing of the staples; the entrance port 40' to the working channel 40 (see FIG. 5); the proximal end of the insertion tube 24; and the cable to the endoscopy suite 42. Not seen in FIG. 2 is the control lever for indexing the cartridge after each array of staples is fired, whish is located on the back side of the handle opposite the staple firing levers.

Figure 3A:
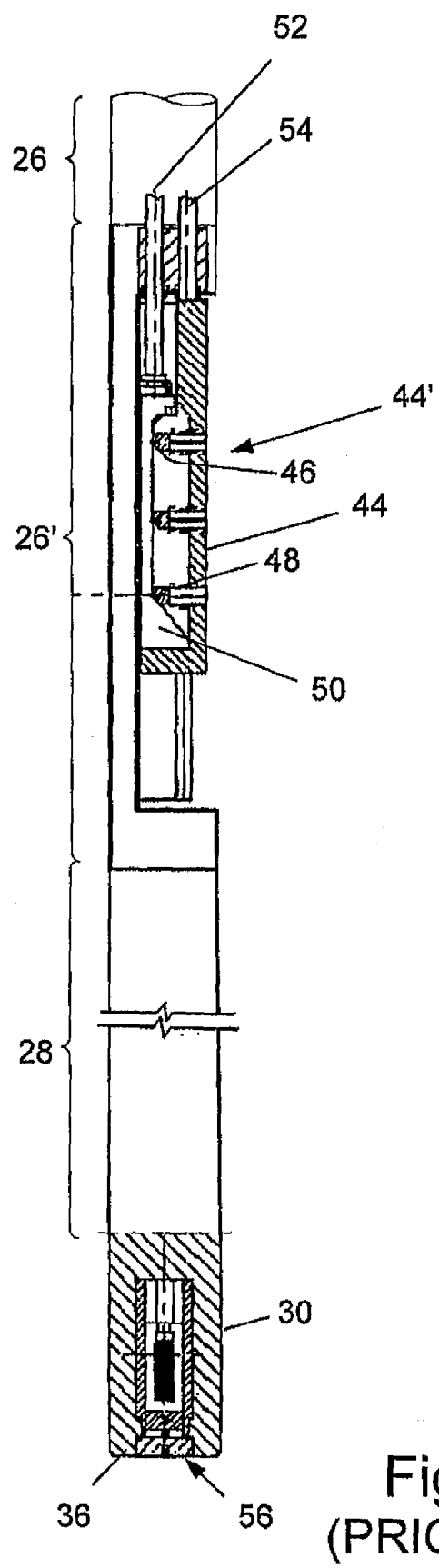
FIG. 3A schematically illustrates the fixed portion and the articulation distal portion of the prior art GERD endoscope, showing the components of the stapler assembly.

In FIG. 3A is shown the distal portion of the insertion tube of the GERD endoscope described in WO01/67964. The insertion tube in this endoscope comprises a staple deployment system located in a recess 44' in a rigid section 26' that is positioned between articulation section 28 and flexible section 26. The staple deployment system comprises a staple storage facility (cartridge 44) and staple firing mechanism. The stapler deployment system has a side firing design and requires an anvil which is located on distal face 36 of the endoscope. The anvil is part of an anvil module 56 located in a recess in the distal tip 30. Both the stapler cartridge 44 and the anvil module 56 are preferably replaceable.

The staple and storage firing mechanism comprises staple cartridge 44 containing one or more (three are shown) arrays of staples 46. The staples are fired by pulling firing cable 52 and the attached cams 50 (located in the cartridge) proximally thus forcing staple pushers 48 to move side wards and pushing the staples out of the cartridge 44. Numeral 54 designates the indexing mechanism used to ready the next array of staples for firing by moving them into position opposite the anvil.

The articulation section 28 is similar in design to that of conventional endoscopes, but possesses several unique features. Firstly, in order to simplify the alignment procedure and at the same time achieve maximum accuracy, a two-way articulation design is preferred, although endoscopes using four-way articulation sections are also available. This generally means that the articulating section is constrained to bend in one plane only. Secondly, the device is able to bend up to 270° in order to carry out the required medical procedure, which is further than in conventional endoscopes. Finally, the articulating section is strong enough to provide a significant force against the tissues during fundus distension, clamping, and stapling (as described in WO 01/67964, with reference to the illustrative surgical procedure).

Figure 3B:
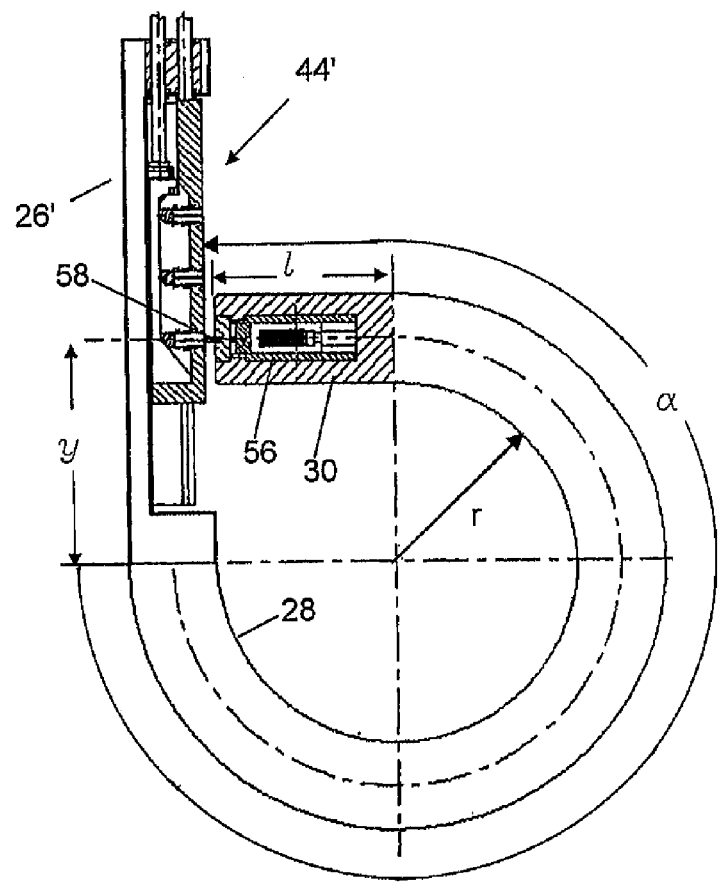
FIG. 3B schematically illustrates the articulation of the prior art GERD endoscope of FIG. 3A through its maximum bending angle.

FIG. 3B schematically shows the device of FIG. 3A in a fully articulated position. The articulation section 28 has been bent through bending angle α using fixed radius of curvature "r". The values of radius "r" and the length of the articulation section are determined by the fixed values "l" (length of the distal tip section 30) and "y" (the distance from the position at which the stapling is to be carried out to the interface of the rigid section 26' and the articulation section 28 of the endoscope) in such a way that articulation of the device completely brings the two parts of the stapler assembly essentially into alignment. Final alignment is aided by various means (not shown in any of the figures) such as an ultrasound system (best described in WO02/068988) and a special configuration of the matching faces of the anvil unit 56 and cartridge 44 (best described in WO2005/115255). When the anvil has been brought into correct working relationship opposite the cartridge screws 58 that are stored in anvil unit 56 are advanced through the tissue pressed between the cartridge and anvil into matching bores in the cartridge to provide exact alignment and distance and to clamp the two parts of the stapler together so that sufficient force can be applied when firing the staples to insure that the legs of the staples enter the recesses on the anvil and curl properly.

Figure 4:
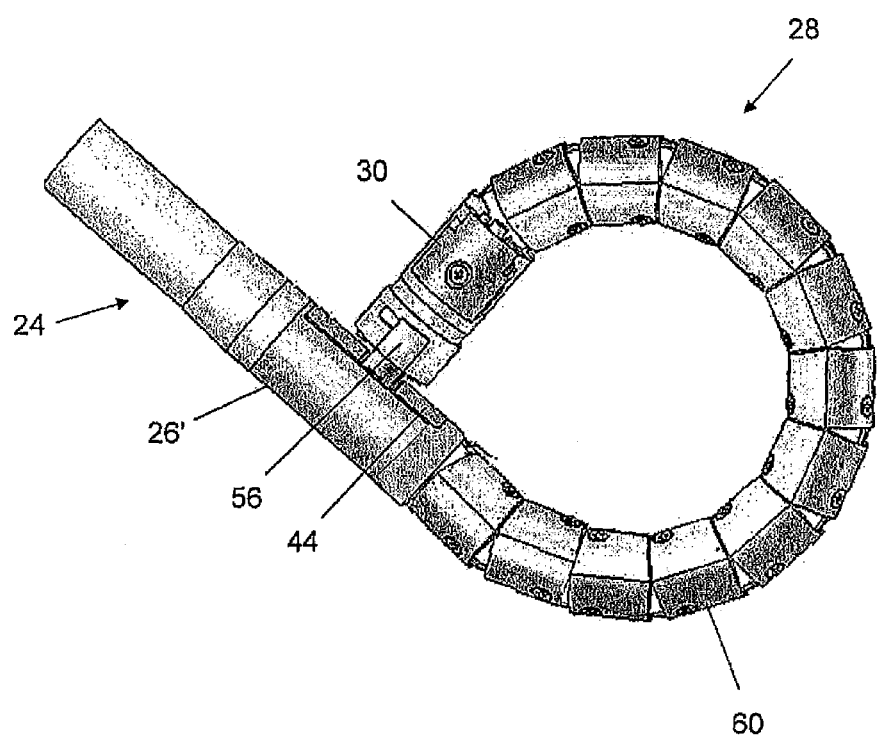
FIG. 4 shows a preferred embodiment of the articulation section of the prior art GERD endoscope in its fully bent configuration.

In FIG. 4 is shown the preferred embodiment (described in WO2006/033109) of the articulation section 28 of the GERD endoscope in its fully bent configuration. In the embodiment shown, articulation section 28 comprises ten identical vertebrae 60 and two more vertebrae at each end that are linked together end-to-end in a chain-like fashion. The two end vertebrae are nearly identical to the others except that the distal end of one and the proximal end of the other one are adapted to connect to distal tip 30 and rigid section 26' of the insertion tube 24 of the endoscope respectively.

The articulation section of the GERD endoscope is designed to provide two-way articulation through an angle of about 270 degrees. That is, as shown in FIG. 4, the articulation section can be bent in one direction in a plane that contains the longitudinal axis of the endoscope until the distal tip is brought to a position opposite the rigid section in the shaft of the endoscope. When in this position the anvil unit 56 and the cartridge 44 are said to be in correct working relationship.

Figure 5:
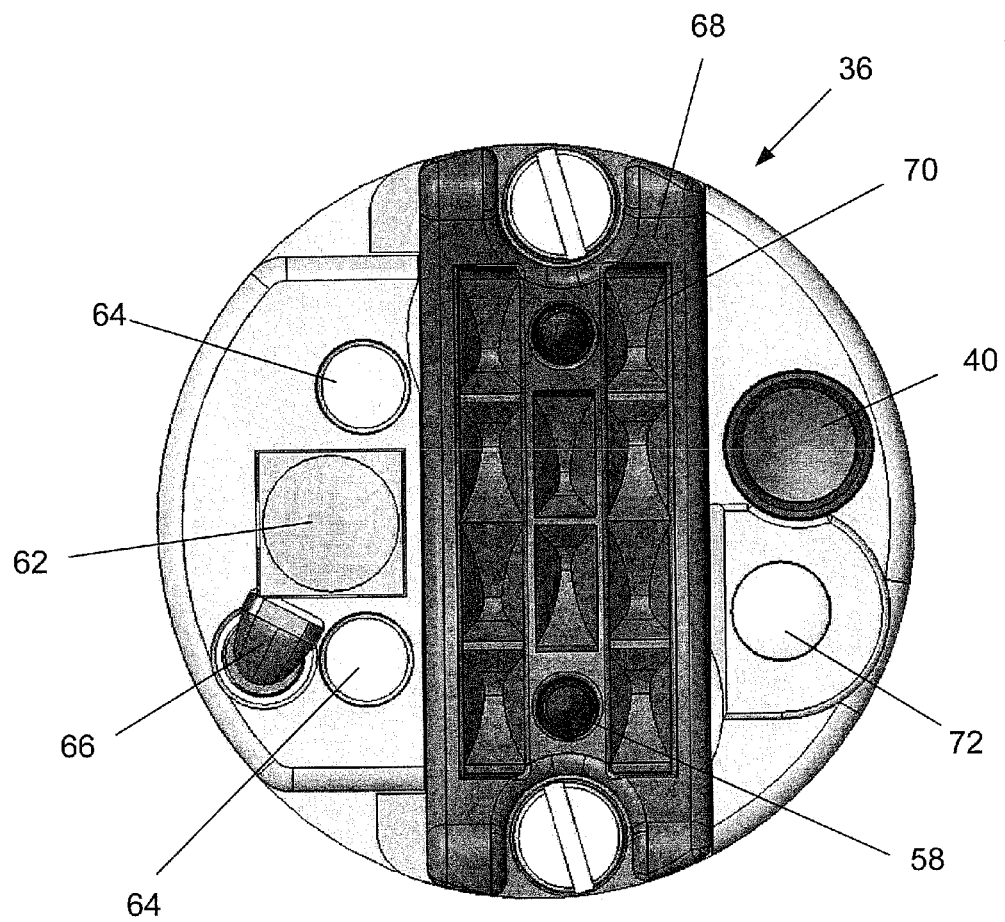
FIG. 5 schematically shows the distal face of the prior art GERD endoscope.

FIG. 5 schematically shows a typical arrangement of the distal face 36 of the GERD endoscope. Shown in the figure is an imaging channel is 62. Numeral 64 represents illumination fibers and numeral 66 designates a nozzle for spraying water or air to clean the objective lens of the camera. One imaging method that can be used is to place a miniature electronic camera unit (described in detail in WO2005/002210 and WO2005/115221) at the distal end of channel 62. Placement of imaging means at the distal tip assists in guiding the device to the desired position in the body lumen and allows imaging of the area during the performance of the surgical procedure. The endoscope may contain two or more separate optical channels that produce two or more distinct views, e.g. a second optical imager can be provided to view through a clear portion of the stapler and will show the staples as they are passed through the tissue and bent closed. Various embodiments of suitable endoscopic optical systems are described in WO02/24058.

Numeral 68 designates the anvil unit face; numeral 58 designates the alignment/locking screws, which are contained in the anvil unit; and numeral 70 designates the depressions for curling the legs of the staples when they are ejected from the cartridge. Numeral 72 designates an ultrasound transducer or reflector that is part of the alignment system. A working channel for introducing surgical tools, suction, or irrigation is shown at 40. The skilled person will understand that other options can be provided and other configurations are allowed depending on the requirements of the endoscopic procedure to be performed. For example, more than one working channel 40 can be provided.

The GERD endoscope is a very robust endoscope that has been designed for multiple uses and to perform medical procedures that require the application of considerable force, e.g. when firing the staples. Typical diameters of a GERD endoscope are 11-16.5 mm.

Figure 6:
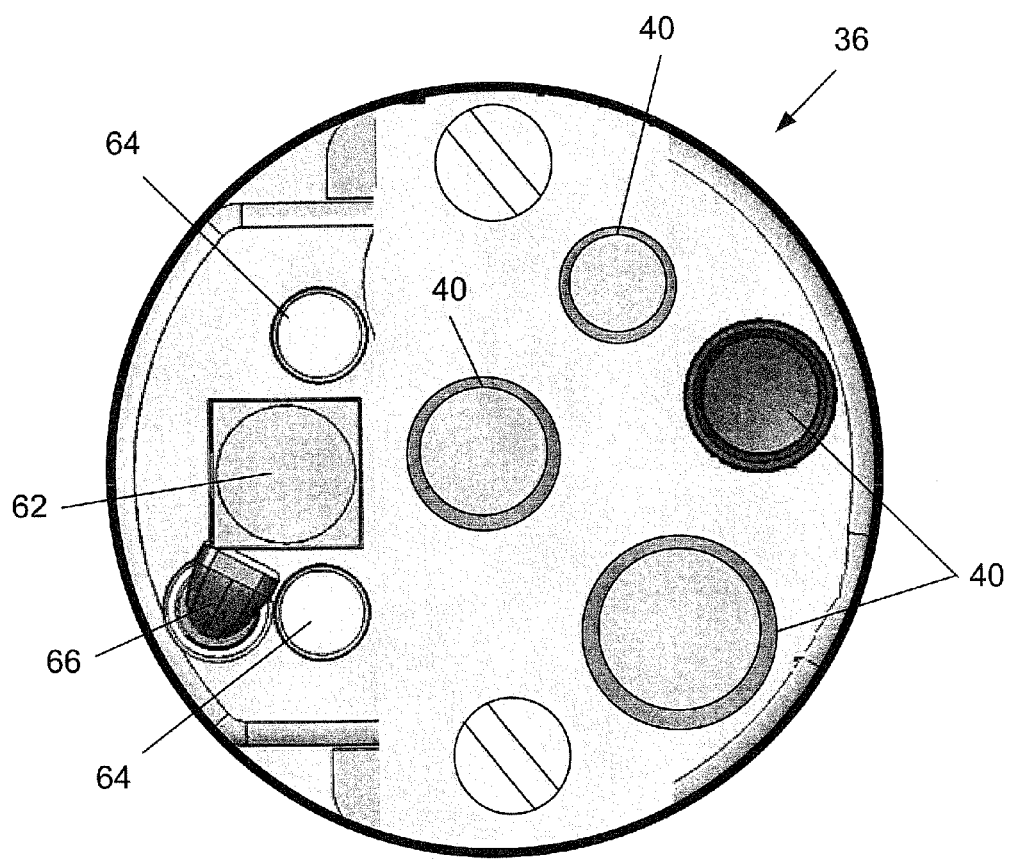
FIG. 6 schematically shows the distal face of the prior art multiple working channel endoscope.

(b) Working Channel Endoscopes:

The endoscopic device called a "working channel endoscope" herein has the same basic structure as the GERD endoscope with the exception that there is no stapler unit and therefore no mechanism for staple firing and indexing. Also typically the ultrasound positioning system is not needed, although for some procedures ultrasound imaging may be used. The main feature of these endoscopes is that they have at least one and typically two to five working channels. This feature, in combination with excellent visualization provided by the camera on the distal face and the controlled flexibility of the articulation section, makes these endoscopes versatile tools for carrying out complex procedures that require the simultaneous use of several surgical tools. The overall diameter of the endoscope and the number and diameters of the working channels depends on the requirements of the procedure. FIG. 6 schematically shows the distal face of a multiple working channel endoscope. In this example are shown the camera 62, illumination fibers 64, spray nozzle 66, and four working channels 40 having different diameters. Typical diameters of the multiple working channel endoscope are 2.8 mm with an internal 1.2 mm working channel and up to 16.5 mm with several working channels having different diameters. The working channel endoscope can be sterilizable and used for many procedures or made for a single use only, with a disposal camera or only the camera head being reusable.

c) Baby Scopes

Embodiments of endoscopes having diameters of less than 3 mm to 5 mm comprising distal tip cameras and articulation sections of the same design and capabilities as those of the larger diameter endoscopes that have been developed are known as babyscopes. The baby scopes are usually made to be disposable after a single use.

The baby scopes developed by the applicant of the present invention are distinguished from currently available small diameter endoscopes by the use of the video camera. The prior art scopes of this type depend on the use of fragile fiber optics to transfer the image gathered by an objective lens from the distal tip to proximal imaging means. Because of the breaking of the optical fibers, the endoscopes generally have a very short useful lifetime despite the fact that they are sterilizable, meant to be used for many procedures, and very expensive.

(d) Endoscope with Distal Tip Stapler to Close Holes

This endoscope is designed exclusively for closing holes in biological tissue. The endoscope itself, with the exception of the distal tip is essentially the working channel endoscope described above, with the addition of a cable to move the anvil longitudinally, thereby firing the staples as described hereinbelow. The distal tip is modified to accommodate two basic embodiments of a surgical stapler—the first closing at right angles to the longitudinal axis of the endoscope and the second in the direction of this axis.

Figure 7:
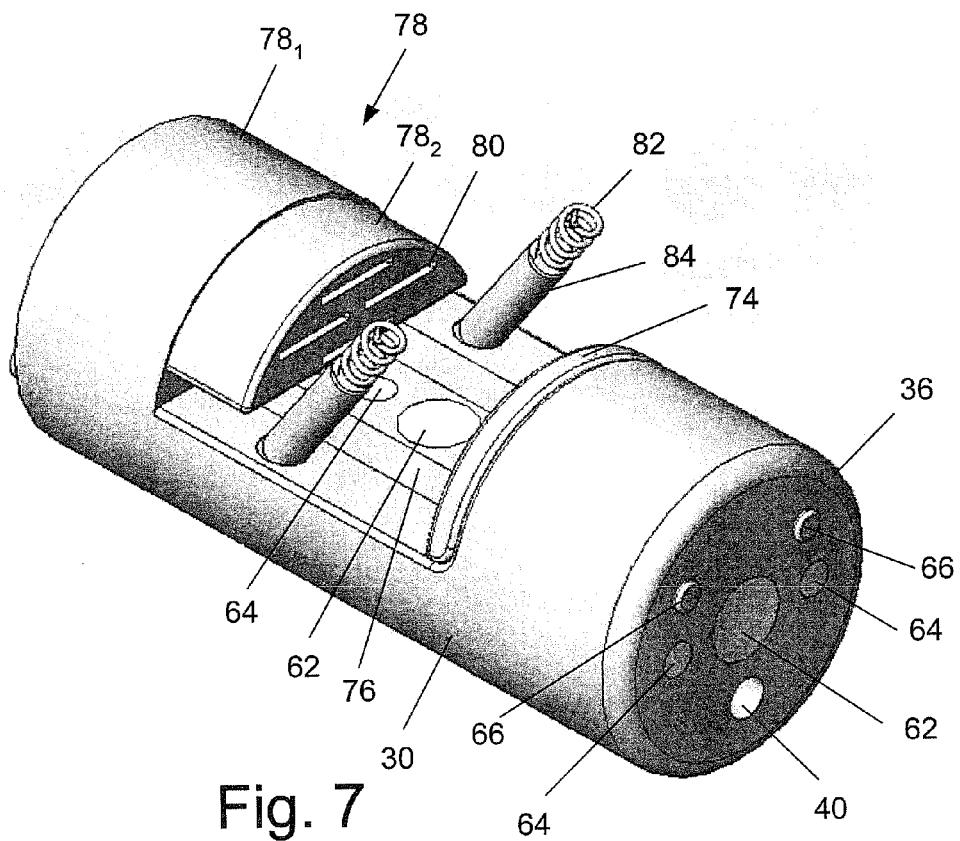
FIG. 7 is a general view from above showing the side closing embodiment of the stapler of the invention located in the distal tip of an endoscope.

FIG. 7 is a general view from above showing the side closing embodiment of the stapler located in the distal tip 30 of an endoscope. On the distal face 36 can be seen a camera 62; the ends of two illumination fibers 64, which provide light to illuminate the field of view of the camera; two nozzles 66 to spray air or water to keep the camera lens clean; and a working channel 40, which can be used to introduce other devices, e.g. ultrasound probe, forceps, needles, etc. Experienced persons will recognize that the configuration and type of elements shown on the distal face in the figures is illustrative only, is not crucial to the present invention, and is related to the particular procedure to be performed and to the accessories provided.

The stapler is comprised of two components: the anvil 74, which is a semicircular flat surface at the bottom of which are attached two legs 76, a staple cartridge 78, which contains an array of staples that exit through slots 80 when the stapler is activated as described hereinbelow. The stapler cartridge is composed of two sections: a proximal section $78_1$, which is either fixedly attached to or manufactured as an integral part of the distal tip, and a distal section $78_2$, which can be slid into proximal section $78_2$ by pushing on the distal face of section $78_2$. In the side closing embodiment of the stapler the cartridge 78 and anvil 74 are located at the proximal and distal ends respectively of a recess cut into the side of distal tip 30. On the floor of the recess are located a camera 62, one or more illumination fibers 64, and water or air nozzles 66 in order to visualize the hole and the tissue grasping procedure as well as to inspect the tissue after the staples are ejected from the cartridge. It is to be noted that here, as in the other endoscopic devices described herein, the illumination for visualization can be provided by alternate means well known to skilled persons, e.g. LEDs. All references in the description herein to illumination fibers is meant to refer to alternate illumination means as well. In order to grasp the tissue, there are provided two screws 82 comprised of stiff wire bent into a spiral shape. The screws 82 pass through overtubes 84 located in channels through the insertion tube of the endoscope. They can be independently advanced, withdrawn, and rotated about their longitudinal axis from the handle at the proximal end of the endoscope.

It is to be noted that here, as in the case of the other endoscopic devices described herein, the illumination for visualization can be provided by alternate means well known to skilled persons, e.g. LEDs. All references in the description herein to illumination fibers are to be understood to refer to alternate illumination means as well.

Figure 8:
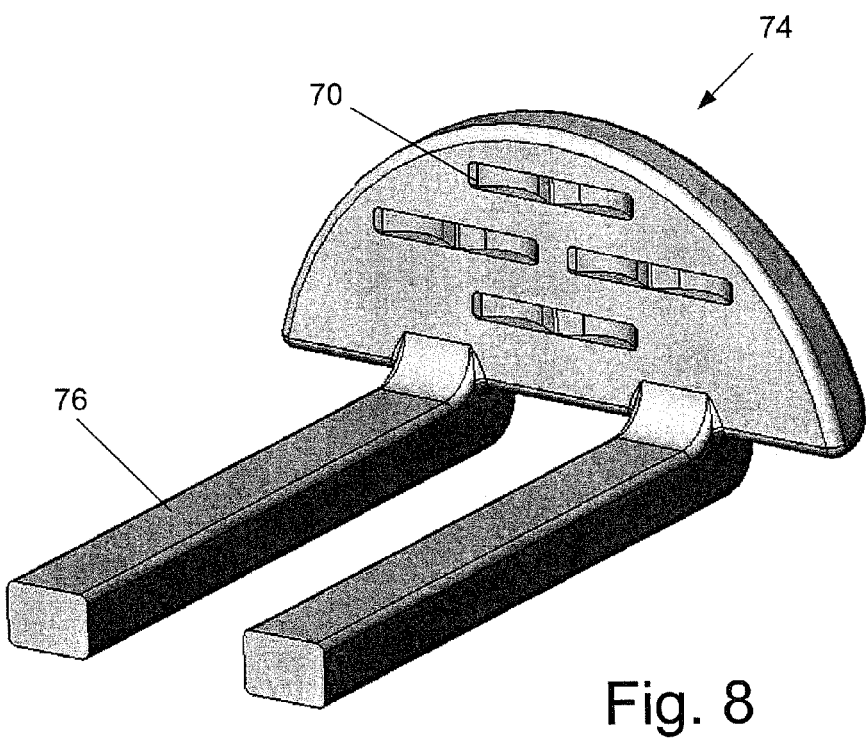
FIG. 8 shows the anvil removed from the endoscope.

FIG. 8 shows the anvil 74 removed from the endoscope. In the figure the depressions 70 into which the legs of the staples enter and are curled when the staples are ejected from the stapler are seen on the face of the anvil. The stapler can be designed to utilize different sizes of staples depending on the diameter of the endoscope and properties of the tissue to be fastened. Typical standard sizes that can be used are 2, 2.5, 3, 3.3, and 4.8 mm metal staples. Biodegradable staples can also be used.

In FIGS. 7 to 10, the diameter of the endoscope is 12-15 mm and the stapler comprises an array of four 4.8 mm staples.

Figure 9:
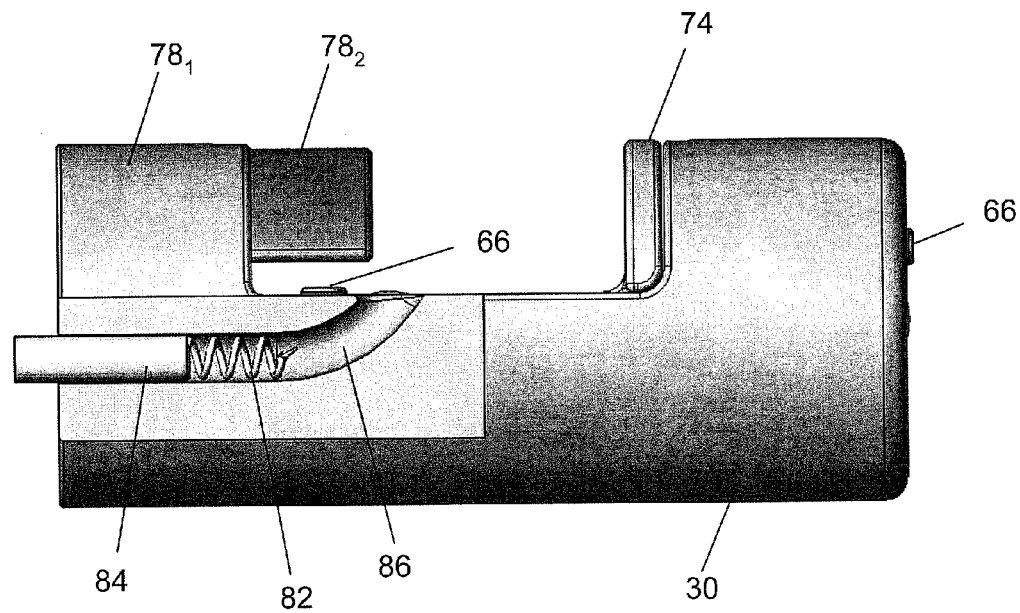
FIG. 9 and FIG. 10 are views with parts of the surface removed to reveal details of the interior of the distal tip.
Figure 10:
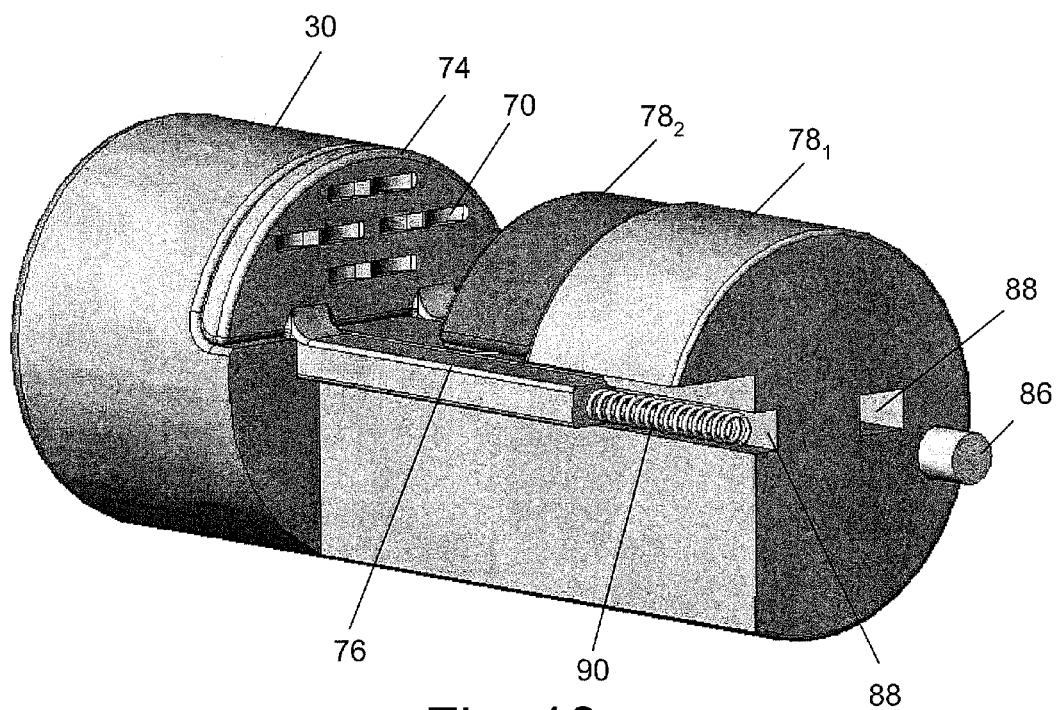

FIG. 9 and FIG. 10 are views with parts of the surface removed to reveal details of the interior of the distal tip 30. In FIG. 9 can be seen the channel 86, through which the overtube 84 and screw 82 are advanced through the length of the endoscope. In FIG. 10 can be seen the slots 88 in which the legs 76 of the anvil can slide. Not shown in FIG. 10 is a cable that is attached to the proximal end of each leg 76, passes through the center of spring 90, and then passes through a channel in the insertion tube of the endoscope to the handle where its proximal end is attached to a mechanism that can be used to pull the entire anvil 74 in a proximal direction. When anvil 74 is pulled in a proximal direction, the proximal end of spring 90 butts up against a stopper (not shown) and is compressed. When the tension on the cable used to pull the anvil proximally is released, spring 90 pushes anvil 86 in the distal direction.

Figure 11:
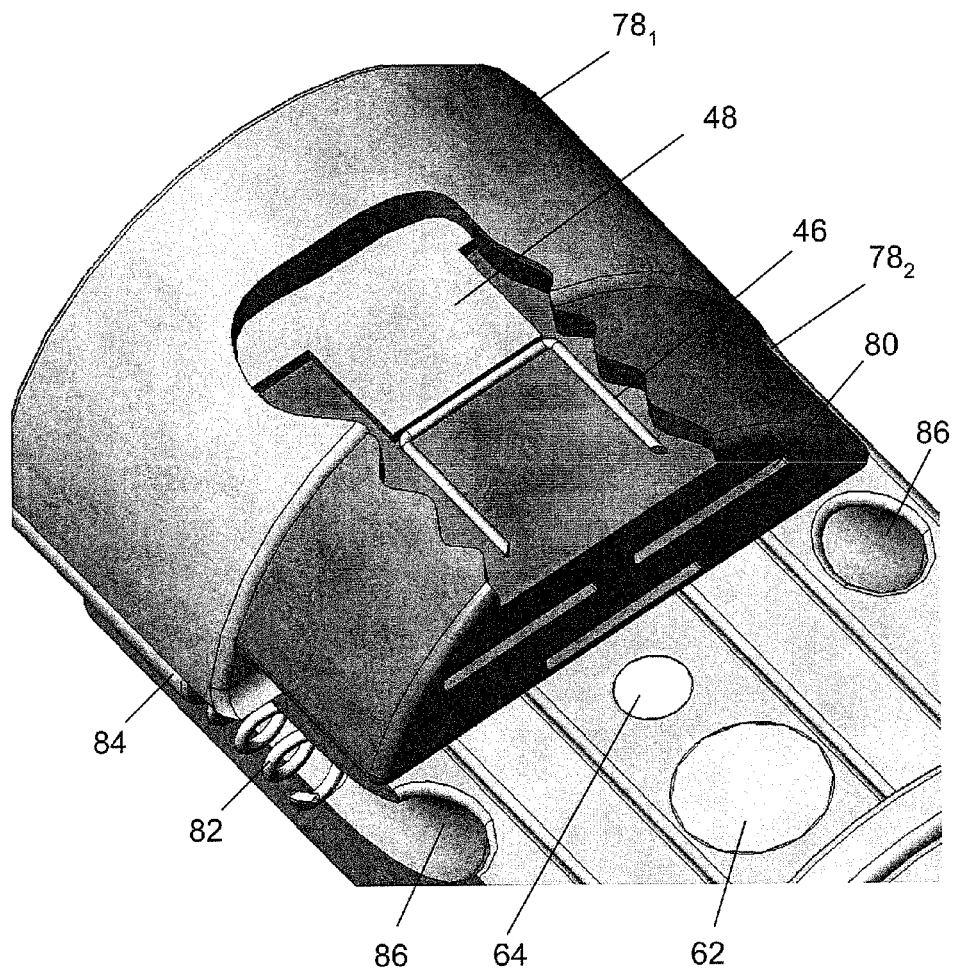
FIG. 11 is a view with part of the wall of the staple cartridge removed to reveal its interior.

FIG. 11 is a top view with part of the wall of the staple cartridge 78 removed to reveal its interior. The cartridge 78 of the stapler of the invention does not comprise any arrangement of cams to actively fire the staples. When the anvil 74 is pulled proximally as described herein above, the face of anvil 74 engages the face of cartridge 78 and pushes distal section 78$_2$ proximally causing it to slide into proximal section 78$_1$. Neither the staple pushers 48 nor the staples 46 move. The staple pushers merely act as a backstop to prevent staples 46 from moving in the proximal direction. In this way the legs of staples 46 are passively forced to exit the distal part 78, of the cartridge through slots 80 and engage the matching depressions 70 on the face of anvil 74. Continued pulling on the cables attached to the legs 76 of the anvil 74 cause more and more of the length of the legs of staples 46 to exit through slots 80 and the legs of the staples start to curl. The process continues until the staples 46 completely exit the cartridge 78 and the stapling process is completed. The cartridge 78 may contain one or more springs to provide a gradually yielding counter force to that exerted by the anvil, thereby aiding to provide a smooth exit of the staples and, if necessary, to return distal section 78$_2$ to its original position as the anvil moves in the distal direction.

Figure 12A:
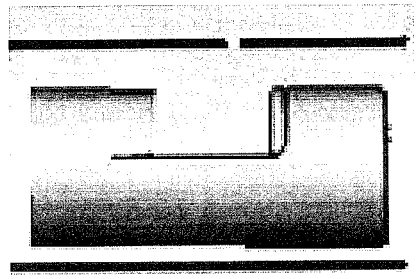
FIGS. 12A to 12F schematically show different stages in the operation of the side fastening embodiment of the endoscopic stapler used to close a hole in biological tissue.

FIGS. 12A to 12F schematically show different stages in the operation of the side fastening embodiment of the stapler to close a hole in biological tissue. The procedure is as follows:

FIG. 12A—The endoscope is inserted into the body cavity using the camera 62 on the distal face 36 for visualization until the hole in the tissue is viewed using the side facing camera 62.

Figure 12B:
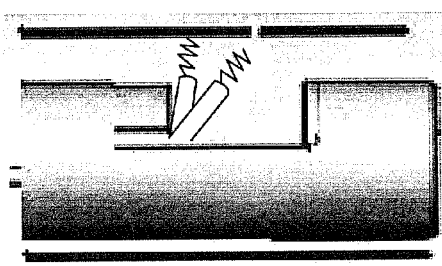

FIG. 12B—The overtubes 84 are pushed out of the channels 86 and the screws 82 are advanced and rotated until they penetrate and grab the tissue on opposite sides of the hole.

Figure 12C:
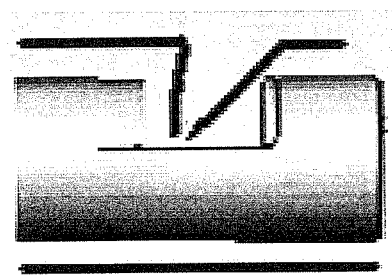

FIG. 12C—The overtubes 84 and the screws 82 with the tissue attached are pulled back into channels 86.

Figure 12D:
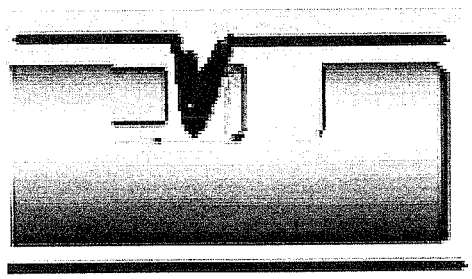

FIG. 12D—The cables attached to the legs 76 of the anvil 74 are pulled causing anvil 74 to move towards cartridge 78.

Figure 12E:
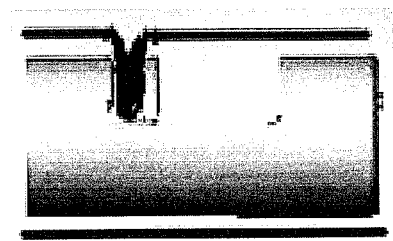

FIG. 12E—The tissue is compressed between the faces of the anvil 74 and the cartridge 78 and moveable cartridge section 78$_2$ begins to slide into fixed cartridge section 78$_1$. The legs of staples 46 begin to exit the slots 80, penetrate the layers of tissue and curl in the depressions 70.

Figure 12F:
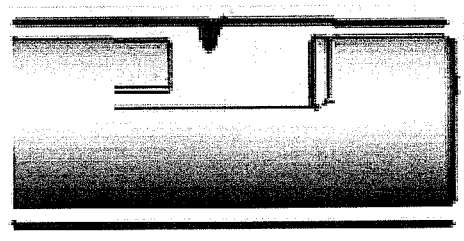

FIG. 12F—The stapling has been completed, screws 82 have been rotated to release their grip on the tissue, the cables attached to legs 76 have been released, and springs 90 have pushed the anvil 74 back to its original position, thereby freeing the stapled tissue. The closed hole is now inspected using the side viewing camera 62 and the endoscope can be withdrawn. If the hole is a large one, another endoscope containing a stapler of the invention can be introduced to the site of the hole and the same procedure followed again to apply a second array of staples next to the first array.

Figure 13:
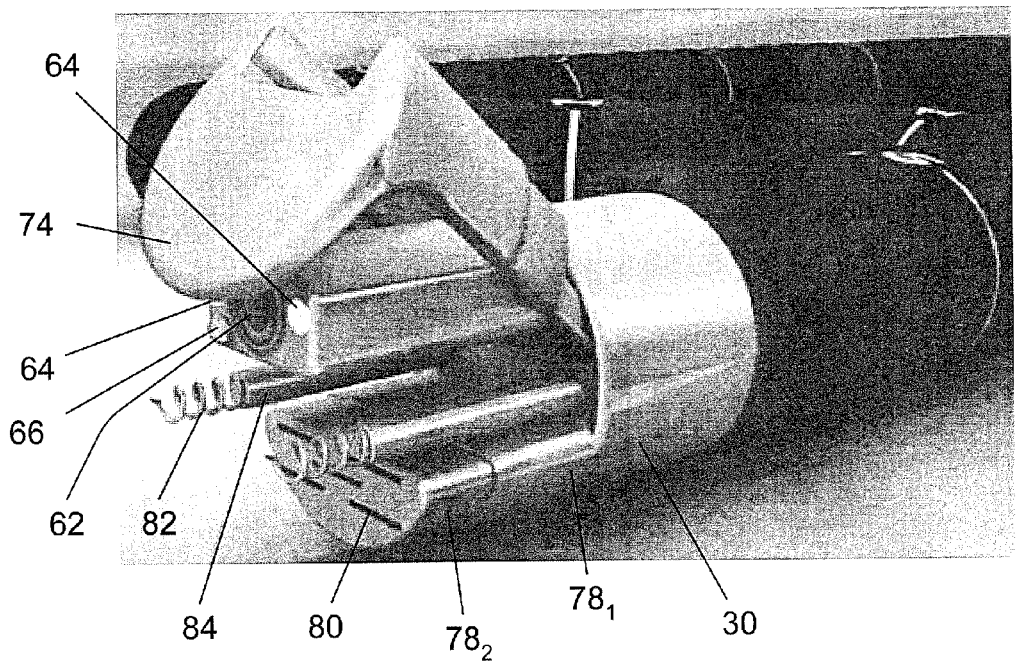
FIG. 13 to FIG. 15 show the front fastening embodiment of the stapler of the invention in the open and closed configurations respectively.
Figure 14:
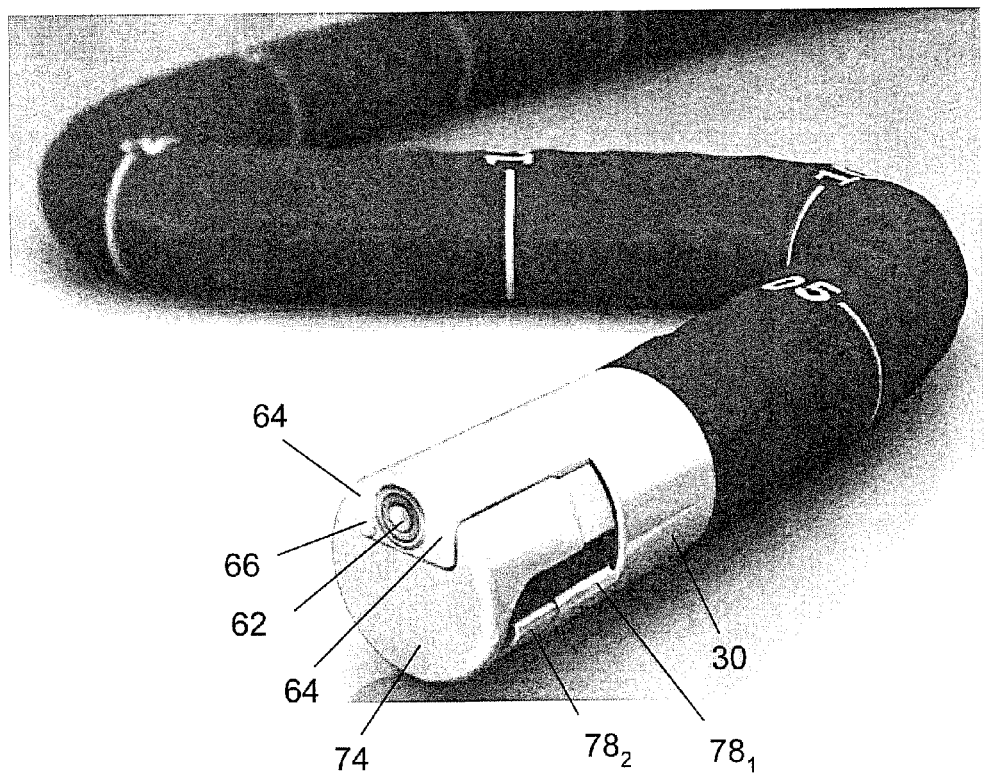
Figure 15:
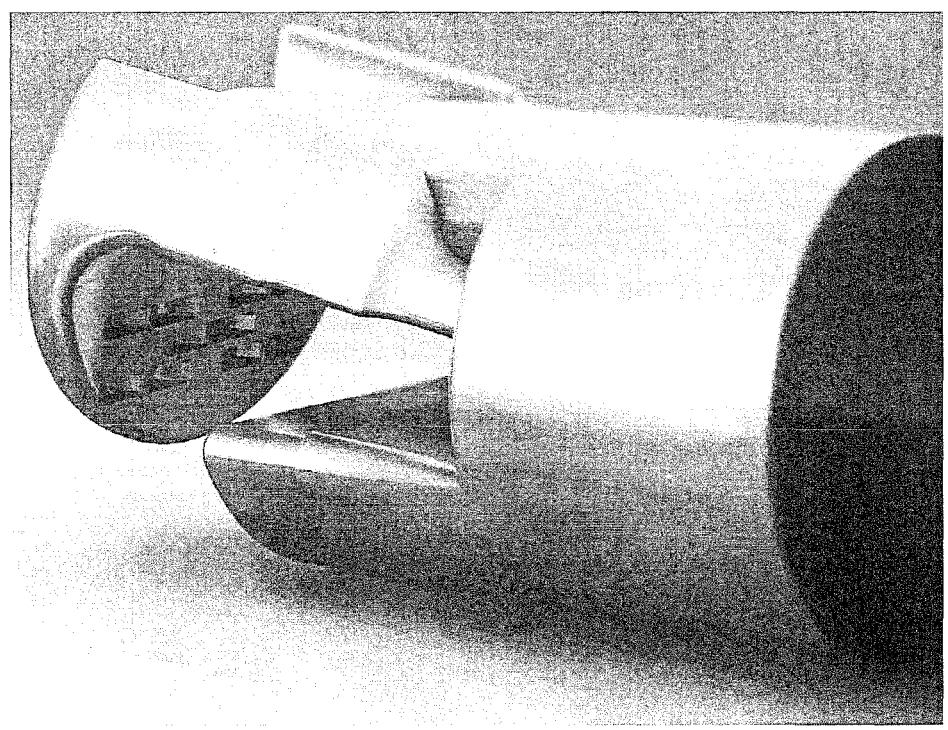

FIG. 13 to FIG. 15 show the front fastening embodiment of the stapler of the invention. Most of the components of the stapler according to this embodiment and its operation are the same as for the side fastening embodiment mutatis mutandis and will not be further described. The major difference between the two embodiments being that in the front fastening embodiment a mechanism activated from the operating handle of the endoscope, e.g. a spring loaded cam system, must be provided to raise and lower the anvil to enable the tissue to be grabbed and pulled between the faces of the anvil and the cartridge for stapling.

FIGS. 16A to 16F schematically show different stages in the operation of the front fastening embodiment of the stapler to close a hole in biological tissue. The procedure is as follows:

FIG. 16A—With the anvil lowered, the endoscope is inserted into the body cavity using the camera 62 on the distal face 36 for visualization. The endoscope is advanced and steered until the hole in the tissue is viewed directly in front of the camera.

FIG. 16B—the mechanism is activated from the control handle of the endoscope causing the anvil to be pushed out of the distal end;

FIG. 16C—as the anvil continues to advance out of the end of the endoscope, it gradually opens;

FIG. 16D—The overtubes 84 are pushed out of the channels 86 and the screws 82 are advanced and rotated until they penetrate and grab the tissue on opposite sides of the hole.

FIG. 16E—The overtubes 84 and the screws 82 with the tissue attached are pulled back into channels 86, the anvil is pulled distally towards the face of the cartridge forcing the anvil down into its lowered position, the tissue is compressed between the faces of the anvil 74 and the face of cartridge 78, moveable cartridge section 78$_2$ begins to slide into fixed cartridge section 78$_1$, the legs of staples 46 begin to exit the slots 80 penetrate the layers of tissue and curl in the depressions 70.

FIG. 16F—The stapling has been completed, screws 82 have been rotated to release their grip on the tissue, the anvil 74 is returned to its open position, thereby freeing the stapled tissue. The closed hole is now inspected using the camera 62 and the endoscope can be withdrawn. If the hole is a large one, another endoscope containing a stapler of the invention can be introduced to the site of the hole and the same procedure followed again to apply a second array of staples next to the first array.

(e) Endoscope with Linear Stapler on Distal End

In some of the procedures described below it is necessary to insert a double line of staples and to cut the tissue between the staple lines, e.g. to bisect the stomach. This is done using an ordinary endoscopic linear stapler. The stapler can be introduced through a working channel in a working channel endoscope. Alternately the stapler can be permanently fixed to the distal end of an endoscope to form a dedicated endoscopic device that also comprises an articulation section and camera on the distal tip. The linear stapler may hold only one array of staples, but preferably it has two or more arrays and it can be indexed to bring the next array into position for firing. Alternately the stapler may comprise a magazine of staples, which are automatically loaded into the array after the previous staples are fired. The arrays of staples are arranged to insert two parallel rows of staples into the tissue held between the two jaws of the stapler. Preferably the stapler also has a knife blade, which can be moved in a slot between the two rows of staples to cut the tissue after the staples have been fired.

(f) Endoscope with Two Linear Staplers on the Distal End

Figure 22A:
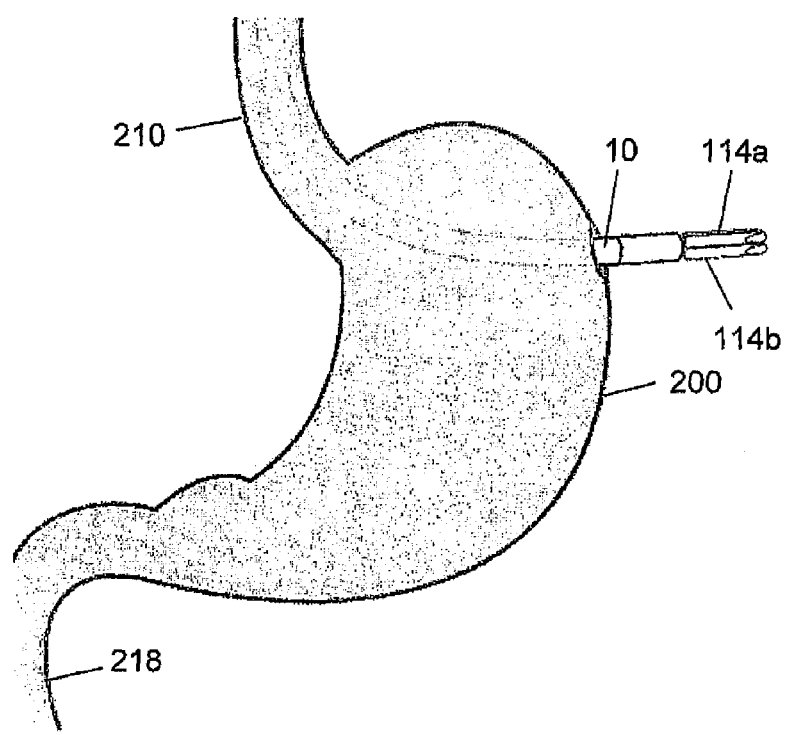
FIGS. 22A to 22G schematically illustrate the steps of another method of performing a mini Gastric Bypass.
Figure 22B:
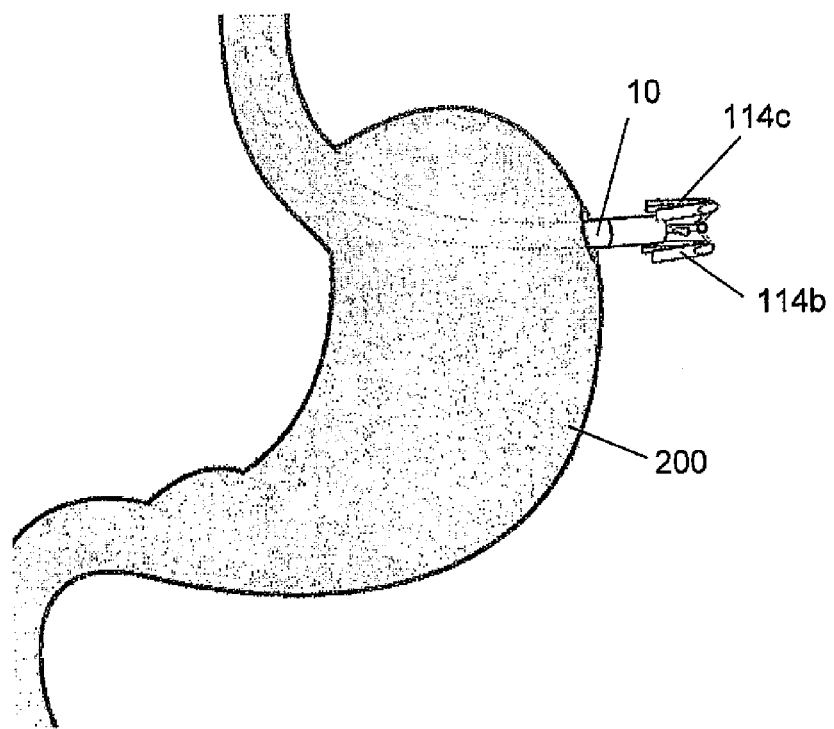

The linear stapler described above is used to simultaneously produce two parallel staple lines. An endoscopic device of the type shown schematically in FIG. 22B is used to produce the staple lines independently. In this case two linear staplers, each of which fires an array comprising one row of staples, is attached to the distal end of the endoscope. The staplers can be introduced through working channels, but are preferably permanently affixed to a dedicated device. The staplers can comprise one or more arrays of staples and at least one of the staplers comprises a knife blade for cutting the tissue parallel to the staples.

The endoscopic instruments described hereinabove can be used to perform endoluminally several types of operations for treatment of morbid obesity that are today carried out either laparascopically or using open surgery. As examples only, embodiments of the invention for inserting gastric bands and performing a mini and a complete Roux-en-Y Gastric Bypass will be presented.

Gastric Banding

Embodiment I

This is a transgastric method of applying a gastric band that creates a very similar anatomic outcome to the currently employed laparoscopic method but is carried out by introducing the band and all the surgical tools endoluminally. In this way the necessity of creating the minimum of five entry ports in the abdominal wall that are required in the laparoscopic method is eliminated. In addition, the procedure may be done under conscious sedation as gastroscopy is done, thus obviating the need for general anesthesia which is the norm in laparoscopic surgery. The procedure is schematically illustrated in FIGS. 17A to 17D.

Figure 17A:
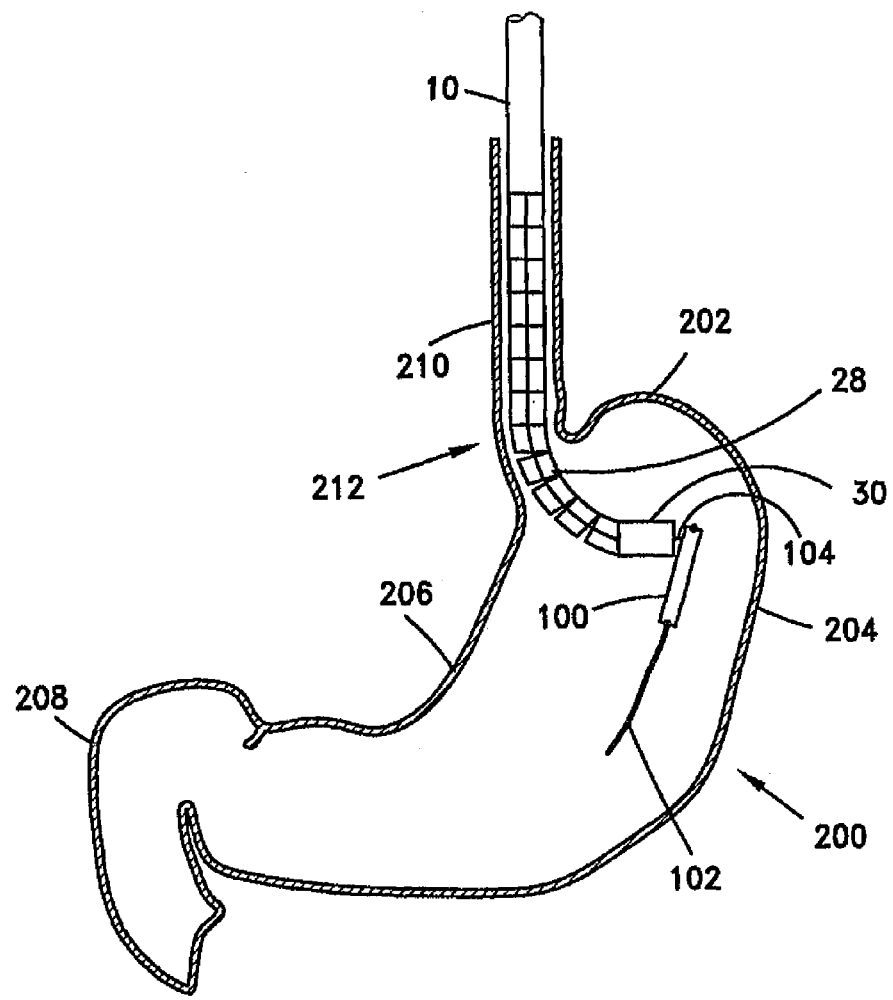
FIGS. 17A to 17D schematically illustrate a transgastric method of applying a gastric band that is very similar to the currently employed laparoscopic method.
Figure 17B:
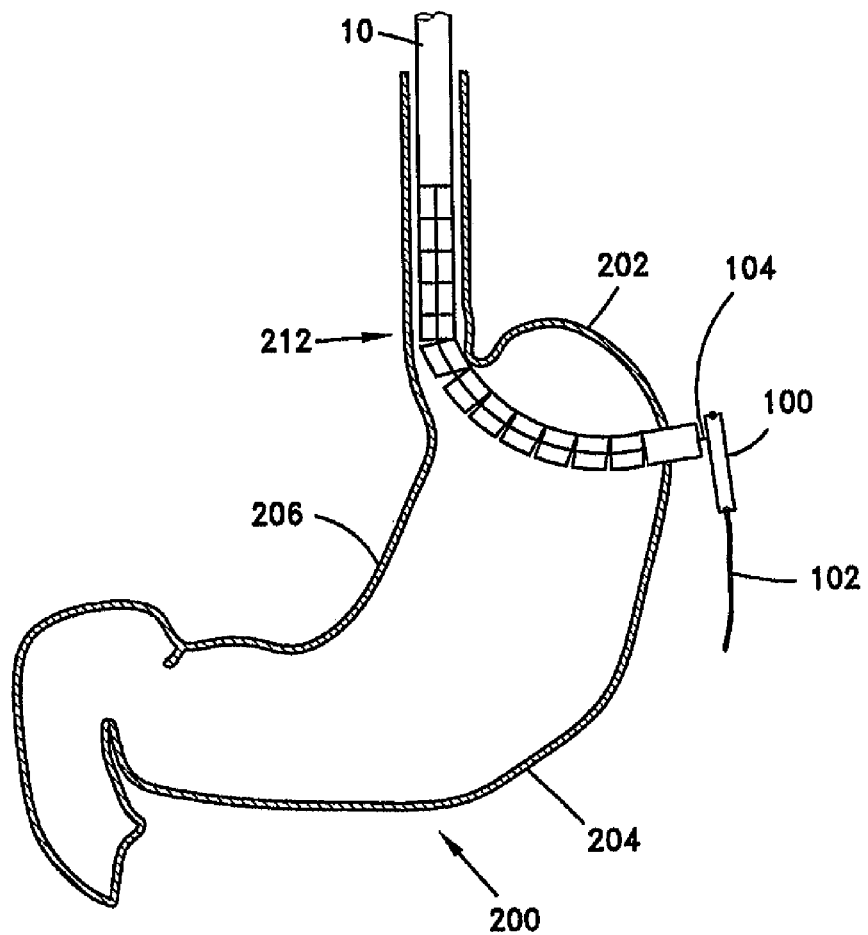
Figure 17C:
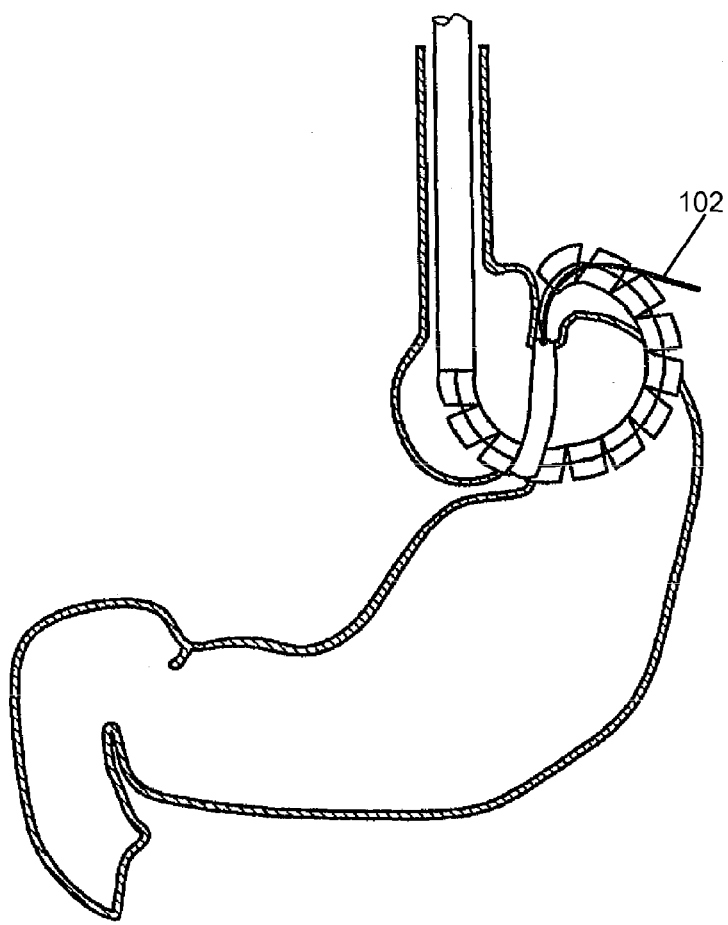
Figure 17D:
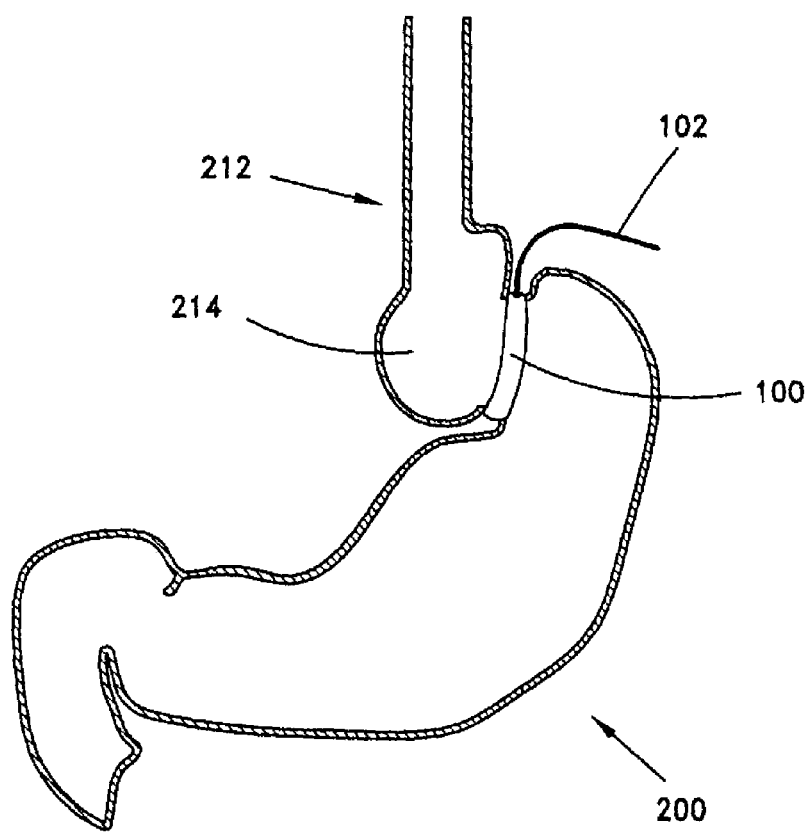

The endoscopic device that is suitable for carrying out this operation is an embodiment of the working channel endoscopes described above. All phases of the procedure are executed using visualization provided by the video camera on the distal tip of the endoscope. The adjustable band 100 is grasped in front of the distal tip 30 of the endoscope 10 by a forceps 104 that passes through one of the working channels. The adjustable band 100 and endoscope 10 are introduced transorally through the esophagus 210 and the lower esophageal sphincter (LES) 212 into the stomach 200 of the patient. Once in the stomach 200 the articulation section 28 is bent to bring the distal tip close to the upper part of the greater curve 204 of the stomach. At this location a hole is made in the stomach wall by means of a surgical cutting tool that has been introduced to the operating site through a second working channel. The distal end of endoscope 10 and attached band 100 are pushed through the hole (FIG. 17B) and the articulation section 28 bent to bring the distal tip 30 near the fundus 202. Various grasper and separator tools are used to slide the band 100 around the upper part of stomach 200. The band 100 is placed at a diagonal from a location on the fundus 202 slightly above the top of the greater curve 204 to a point on the upper part of the lesser curve 206. Grasping and other tools introduced through the working channels are used to manipulate perigastric tissues, e.g. the fat pad, move the band 100 into position, pull the band tight, and attach its two ends together (FIG. 1C). A baby scope may be introduced through a working channel of the endoscope and used to manipulate the band around the posterior side of the stomach under visualization by the distal tip camera of the baby scope. After band 100 is fastened it is released, the articulation section is straightened and repositioned, and the free end of the inflation tube 102 of the band 100 is grasped by a grasping tool and is maneuvered into position and attached to a connection on a port that has been implanted in the abdominal wall of the patient. Finally, the endoscope 10 is withdrawn from the patient. A second endoscope with a front closing stapler mounted on its distal tip is now inserted into the stomach and used to close the hole around the tube 102, after which the stapler is also withdrawn. The result of the procedure is shown in FIG. 17D. Band 100 is wrapped tightly around the stomach forming a small pouch 214 below LES 212. Food can flow from pouch 214 into the lower part of the stomach by passing through a stoma created by the band 100. The diameter of the stoma can be adjusted by inserting or withdrawing a fluid such as air or saline solution from a balloon-like compartment on the inside surface of band 100 via the implanted port and tubing 102.

Gastric Banding

Embodiment 2

Figure 18A:
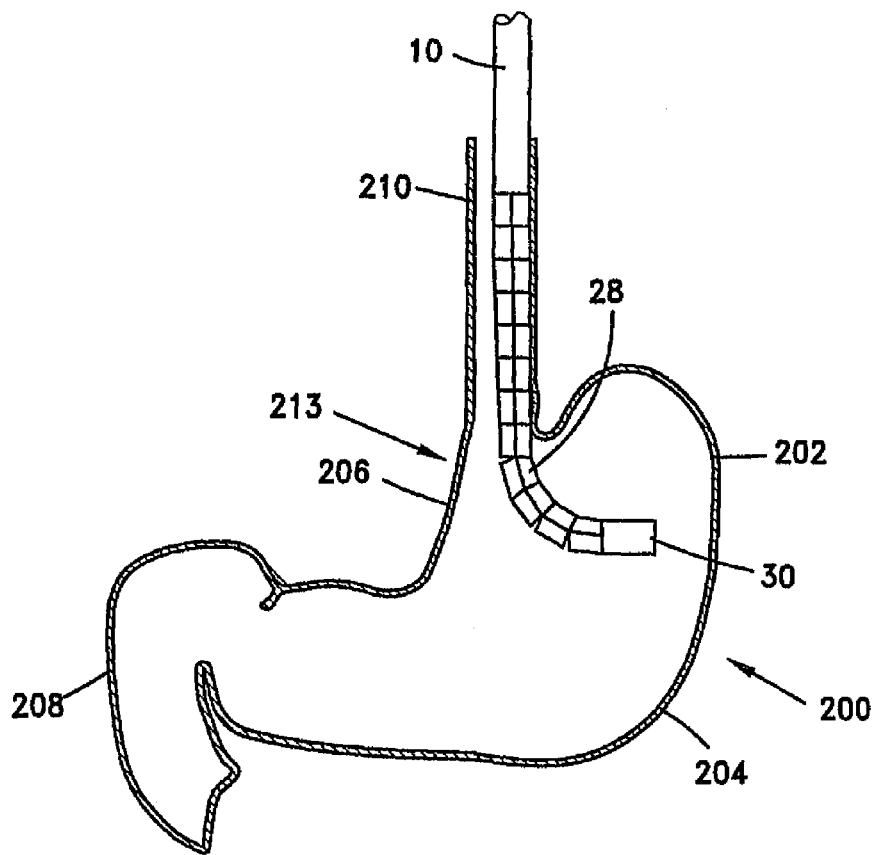
FIGS. 18A to 18G schematically show the steps of another method of inserting a gastric band.
Figure 18B:
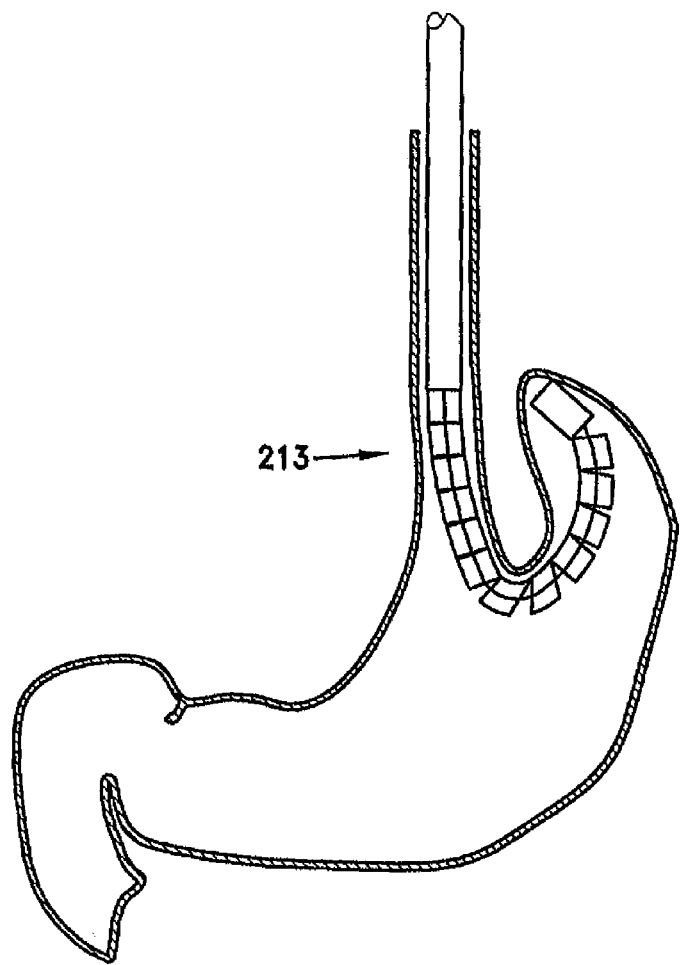
Figure 18C:
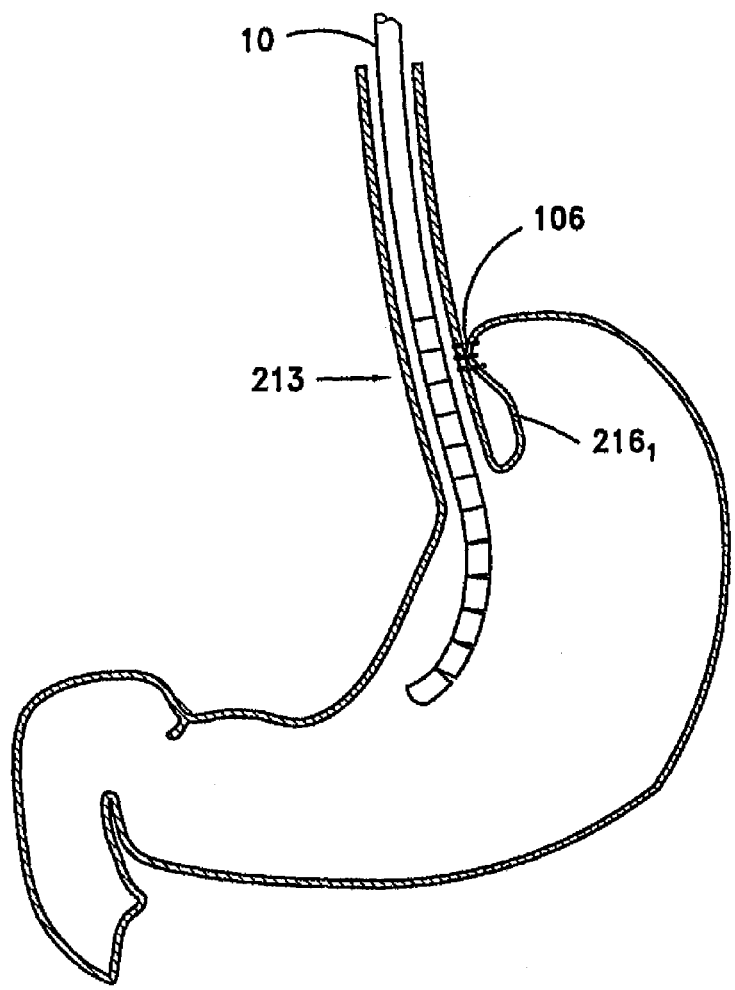
Figure 18D:
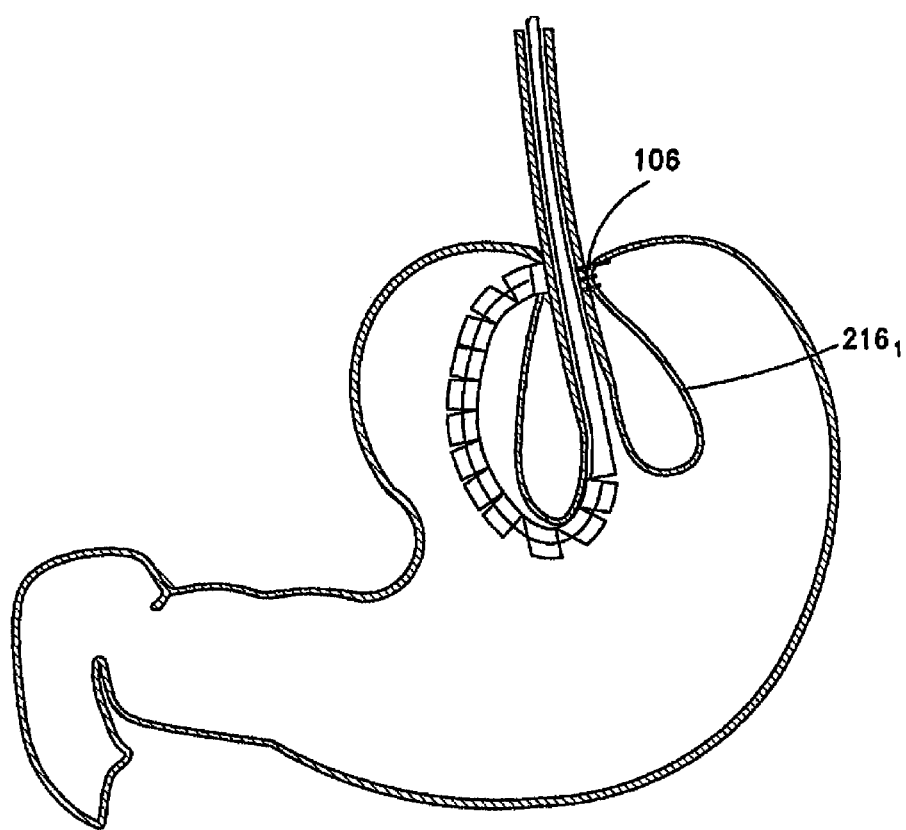
Figure 18E:
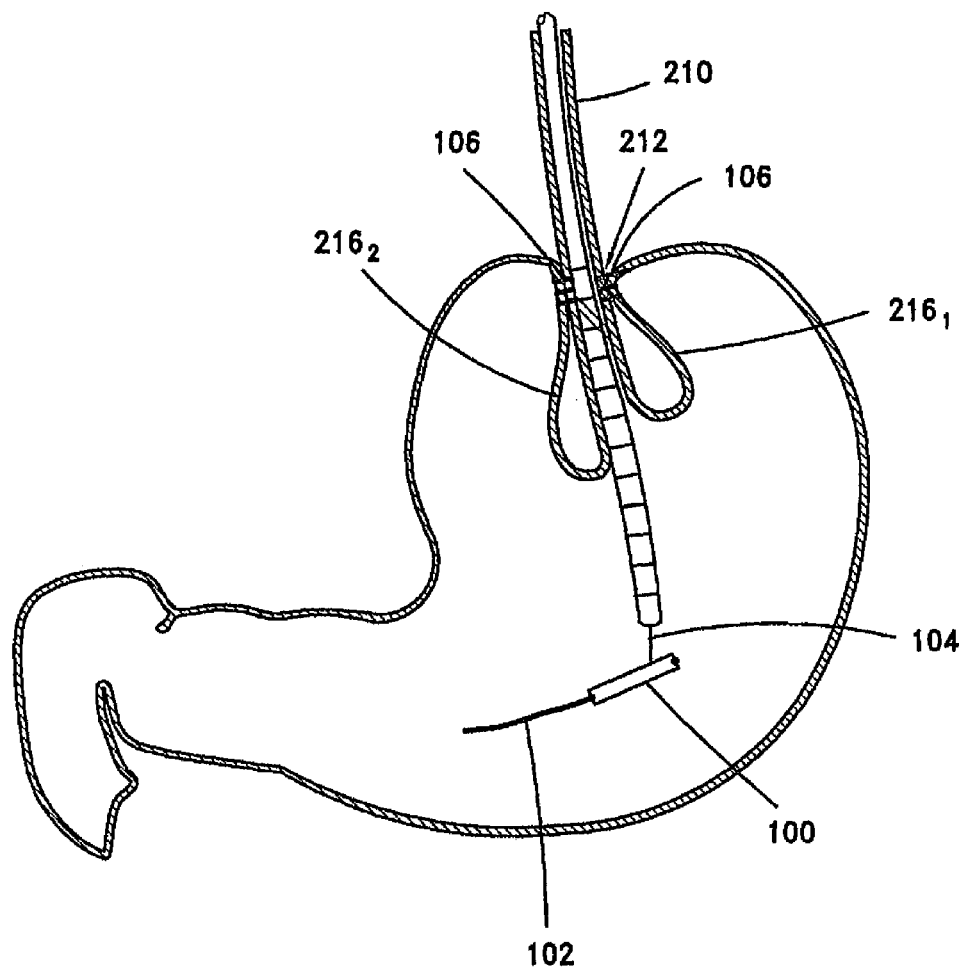
Figure 18F:
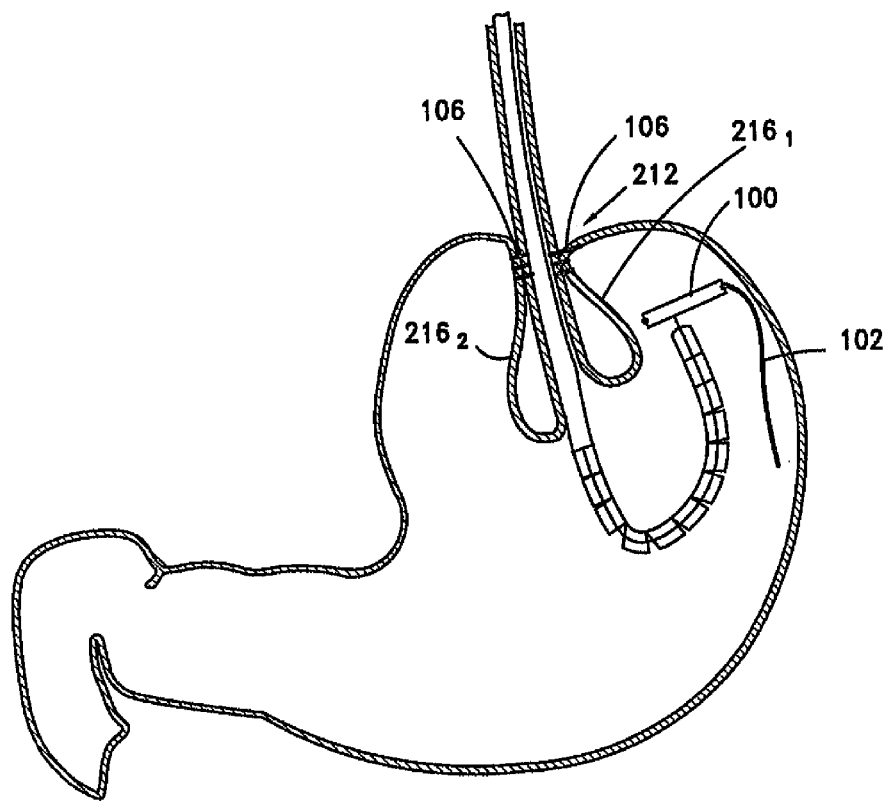

A second embodiment of the invention is based on the use of the GERD endoscope and the method of using it to perform a fundoplication that is described in WO 01/067964. The steps of the method of inserting the gastric band are schematically shown in FIGS. 18A to 18G. The GERD endoscope 10 is first introduced through the esophagus 210 into the stomach 200 and bent so that the distal tip 30 engages the wall of the stomach 200 about at the location where the upper part of the greater curve 204 joins the fundus 202 (FIG. 18A). The articulation section 28 is bent further until the outer side of the stomach wall is folded back and pressed against the outer side of the cardia 213 (FIG. 18B). An array of staples 106 is fired to attach the walls to each other creating a full loop $216_1$. The endoscope 10 (now shown in the FIG.) is then straightened, rotated about 180 degrees and bent and advanced until it contacts the stomach wall along the lesser curvature (FIG. 18C). As before on the other side of the stomach, the stomach wall is raised and the outer wall of the lesser curve is stapled to the wall of the cardia 213 creating full loop $216_2$ (FIG. 18D). This procedure can be repeated to create more than two similar loops if required. The GERD endoscope is now withdrawn from the patient and a working channel endoscope with an adjustable band 100 held in front of it by a grasping tool 104 is introduced through the esophagus into the stomach (FIG. 18E). The articulation section of the endoscope is bent to bring the distal tip and the band close to the upper part of the stomach (FIG. 18F). Using grasping tools the band is wrapped around the outside of loops $216_1$ and $216_2$ and the ends of the band are joined. Sutures or staples may be put around the band or gastro-gastric sutures applied, as is commonly done, in order to prevent migration or slippage.

Figure 18G:
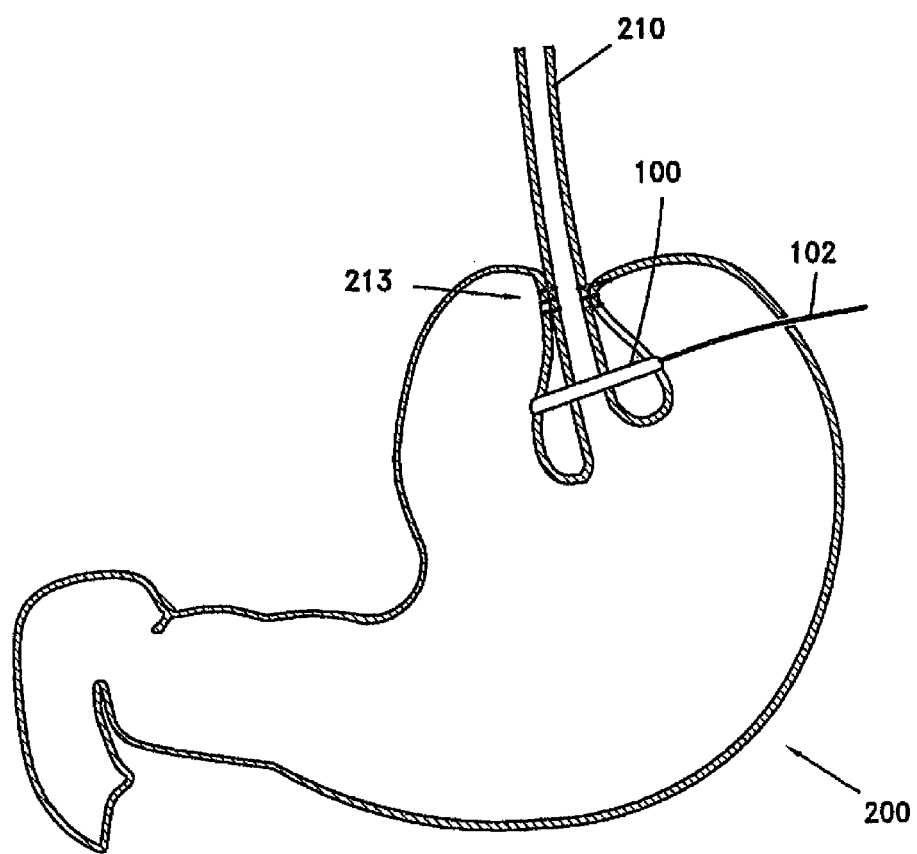

The distal tip of the endoscope is now positioned at the wall of the stomach. A cutting tool is introduced through one of the working channels and a hole made in the stomach wall. The endoscope is pushed through the hole and the free end of the inflation tube 102 of the band 100 is grasped by a grasping tool and is maneuvered into position and attached to a connection on a port that has been implanted in the abdominal wall of the patient. The steps of positioning and connecting inflation tube 102 may be more conveniently carried out by means of a baby scope. The endoscope is withdrawn from the patient and a third endoscope with a front closing stapler mounted on its distal tip is now inserted into the stomach and used to close the hole around the tube 102, after which the stapler is also withdrawn. The result of the procedure is shown in FIG. 18G.

Gastric Banding

Embodiment 3

Figure 19:
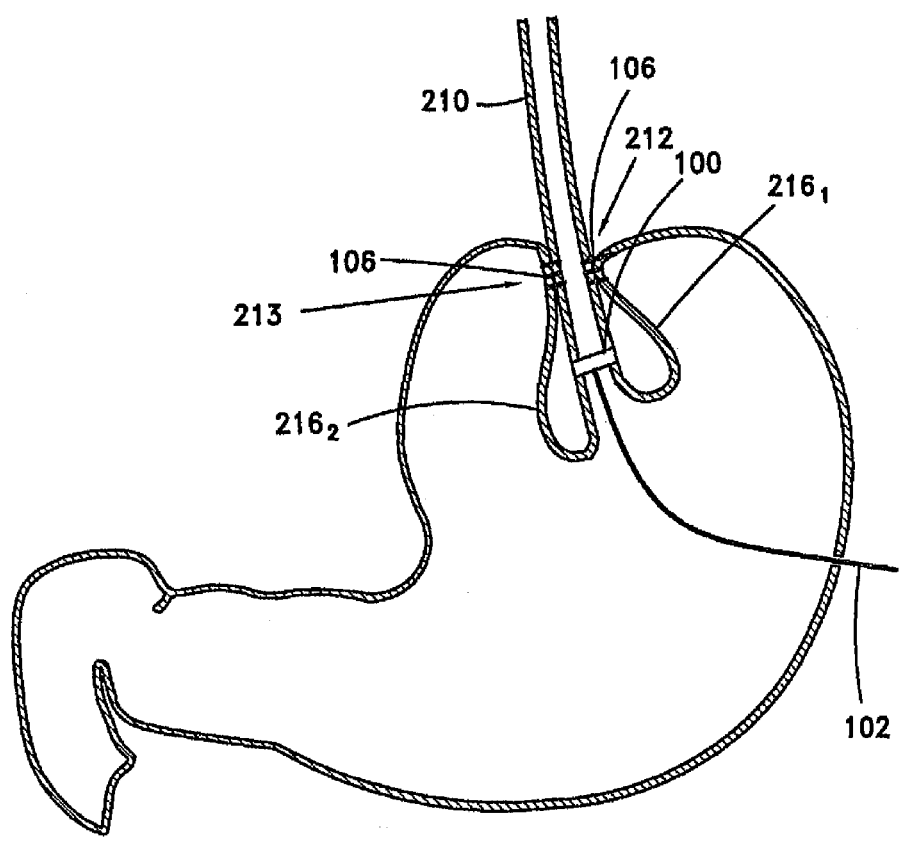
FIG. 19 schematically illustrates the last steps of another method of inserting a gastric band.

Most of the steps of the third embodiment are essentially the same as those of the second embodiment. The steps shown in FIG. 18A to FIG. 18F are identical. FIG. 19 is used to illustrate the final steps of the procedure. Referring now to FIG. 18F, when the articulation section of the endoscope is bent to bring the distal tip and the band close to the wall of the cardia, a cutting tool is passed through a working channel and is used to make a small hole in the lower part of the wall of the cardia 213. Grasping tools passed through the working channel of the endoscope are now used to pull the band out of the stomach through the hole and to wrap it around the outside of the cardia and join the ends of the band together. After the ends of the band are joined, the distal tip of the endoscope is now positioned at the wall of the stomach. A cutting tool is introduced through one of the working channels and a hole made in the stomach wall. The endoscope is pushed through the hole and the free end of the inflation tube 102 of the band 100 is grasped by a grasping tool and is maneuvered into position and attached to a connection on a port that has been implanted in the abdominal wall of the patient (FIG. 19). In this embodiment, the band is held in place around the outer wall of the cardia by the plicated and stapled walls of the stomach. It should be noted that this embodiment can be carried out by stapling the wall of the stomach to the cardia at more than two locations. In addition, it is easier to make the hole and attach the band after the stomach wall is attached on one side only (e.g. as shown in FIG. 18C). If this is done it will be much easier to attach and fasten the band. Also if the second side is stapled after the band is already in place, it can be attached to the cardia such that the band is more tightly held then in the method described above.

Mini Gastric Bypass or Roux-En-Y Gastric Bypass

Embodiment 1

Figure 20A:
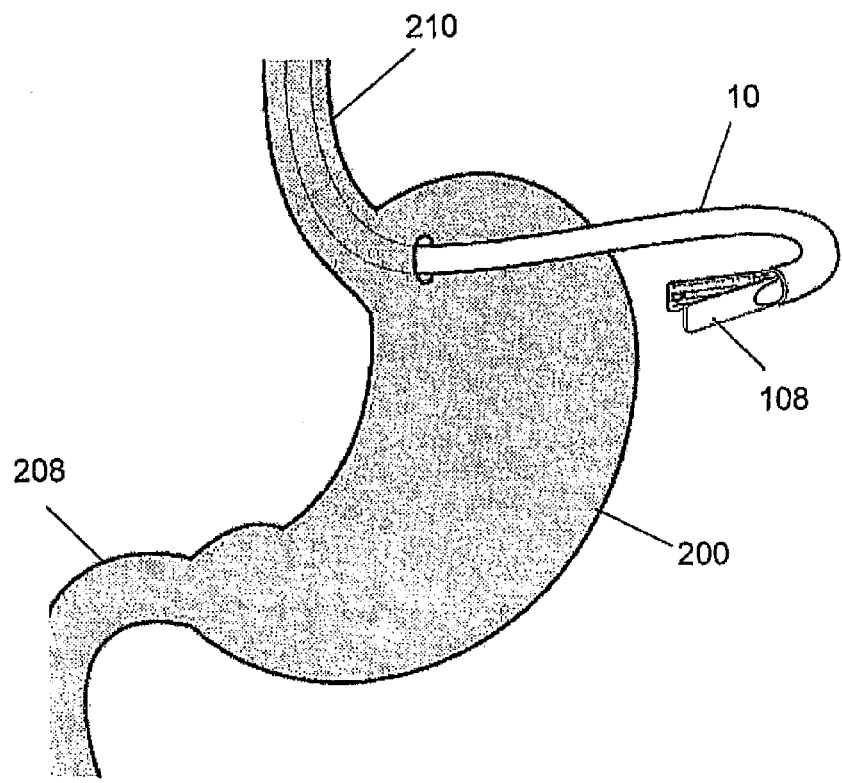
FIGS. 20A to 20E schematically illustrate the steps of performing a mini Gastric Bypass according to the invention.
Figure 20B:
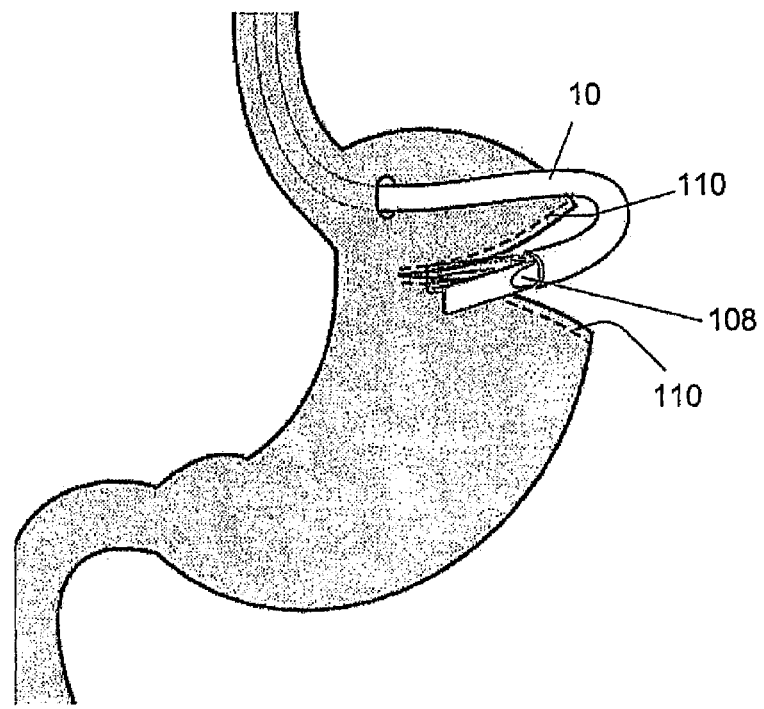
Figure 20C:
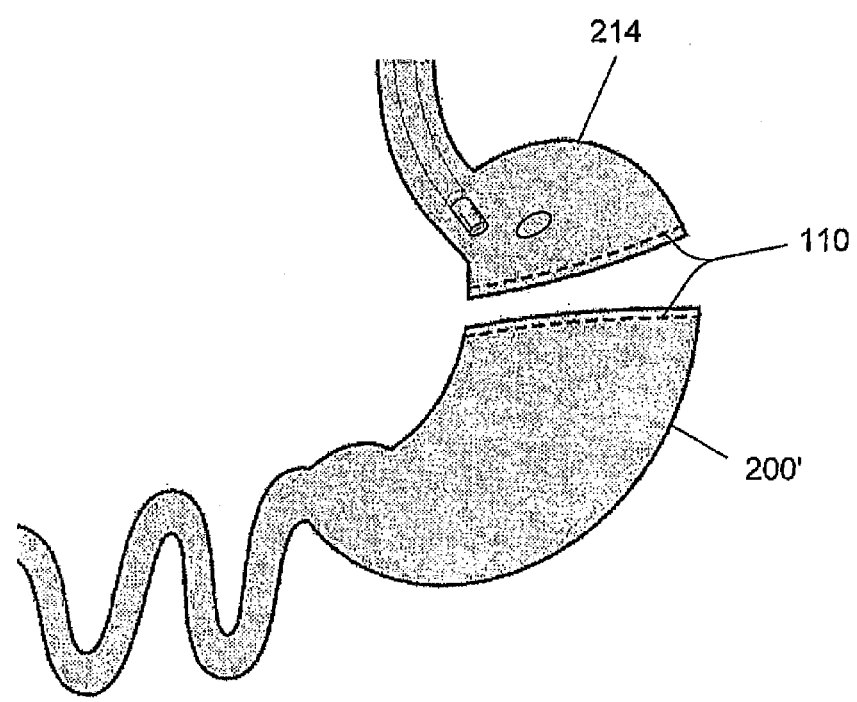
Figure 20D:
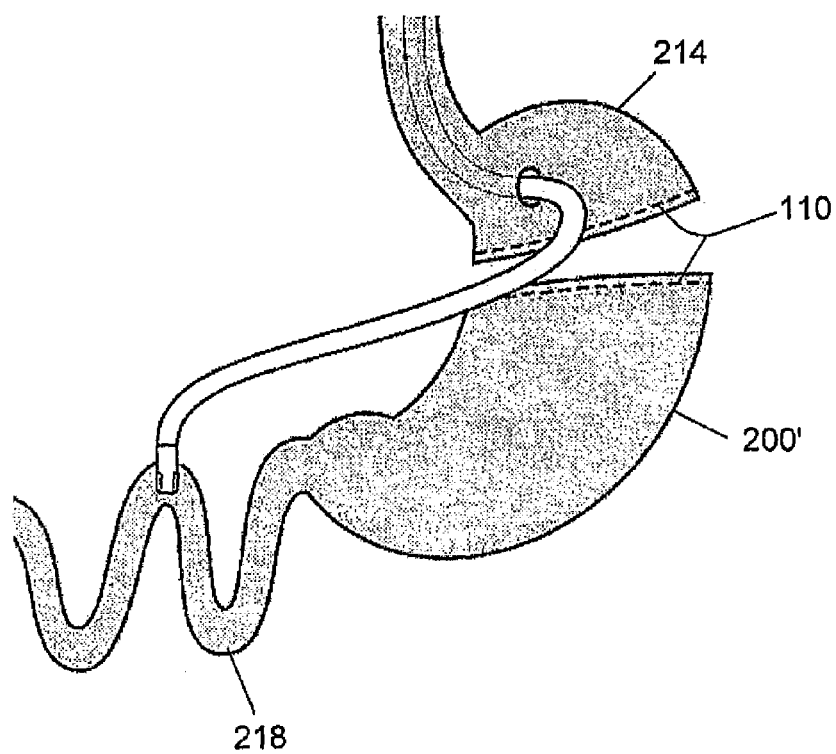
Figure 20E:
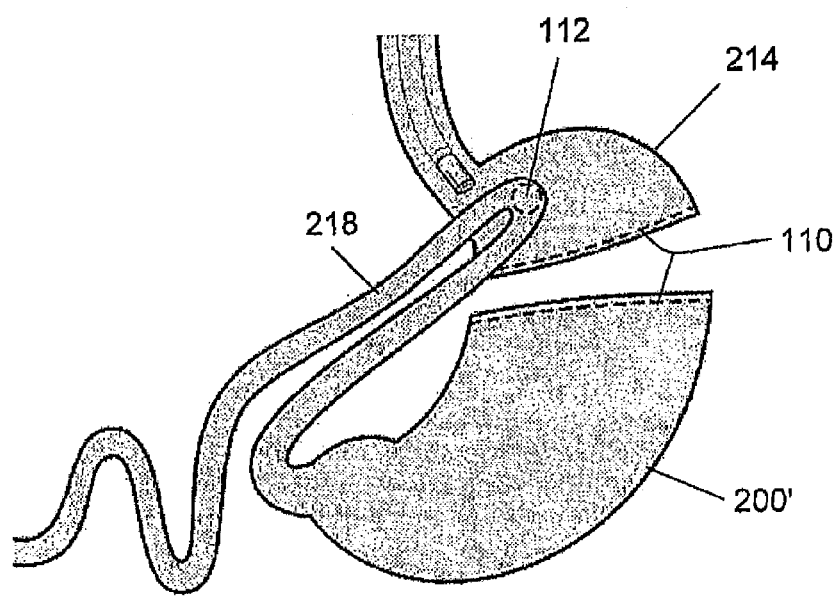

FIGS. 20A to 20E schematically illustrate the steps in performing a mini Gastric Bypass. An endoscope 10 having at least one working channel and a linear stapler 108 that applies two parallel lines of staples and video camera on its distal face is inserted into the stomach 200 through esophagus 210. A cutting tool introduced through the working channel is used to cut a hole in the wall of the upper part of stomach 200. The endoscope is then pushed transgastrically and articulated so that the jaws of the stapler face the exterior of the stomach (FIG. 20A). The jaws of the stapler are then closed grabbing the tissue and an array of staples are fired to make a double line of staples 110 below the hole in the stomach wall. A surgical knife (not shown) in the stapler is activated to cut the tissue between the lines of staples. The jaws of the stapler are then opened, the endoscope is moved forward until more of the stomach is between the walls, the jaws are closed, a second array is fired to lengthen staple lines 110 and the tissue is again cut (FIG. 20B). This procedure is repeated as many times as necessary until the stomach has been bisected into two parts, an upper small pouch 214 and a lower part 200' (FIG. 20C). The endoscope is now maneuvered until it is in a position that a grasping tool can be used to grab the intestine 218 (FIG. 20D). In order to create a mini gastric bypass, the endoscope is now pulled in the proximal direction until the grabbed part of the intestine is pulled into the hole in pouch 214. A hole is now made in the wall of intestine 218 and it is connected to pouch 214 by conventional means, e.g. an anastomosis button 112, staples, or clips (FIG. 20E). The procedure has been described as if carried out using a single endoscope, however it is clear that more than one dedicated endoscope can be used to perform different steps in the procedure.

Once the gastric pouch has been created using the minimal invasive method of the invention (FIG. 20C), the physician may choose to create a mini gastric bypass as described in the last paragraph, or alternatively utilize any minimally invasive approach that he wishes to cut and connect a small intestine Roux limb in order to complete a Roux-en-Y procedure. It is important to note that sometimes the liver may cover part of the stomach, hence obstructing the path for stapling and cutting the stomach. This obstacle is overcome by using one of the working channels of the endoscope to place a balloon having a cylindrical or similar shape with a hole in its middle between the liver and external stomach wall. Inflating the balloon will separates the two organs and creates a clear path for the endoscope and the stapler. Near the end of the procedure the balloon is deflated and withdrawn with the endoscope through the incision into the stomach and out of the patient's body.

Mini Gastric Bypass or Roux-En-Y Gastric Bypass

Embodiment 2

Figure 21A:
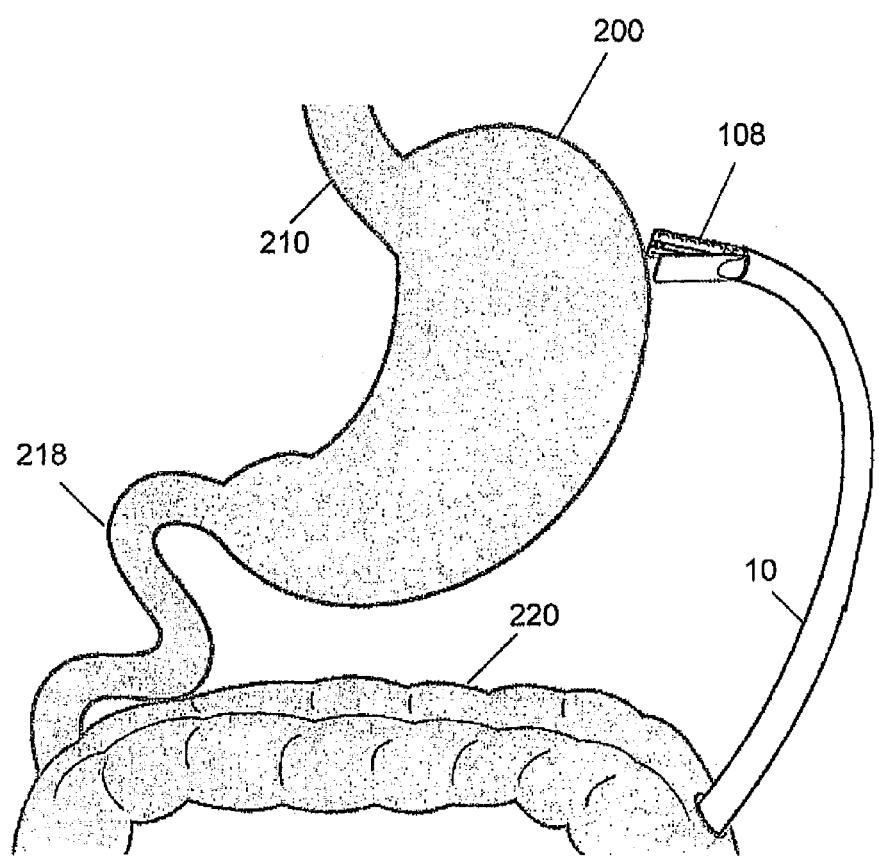
FIGS. 21A to 21C illustrate a second way of endoscopically performing a mini Gastric Bypass.
Figure 21B:
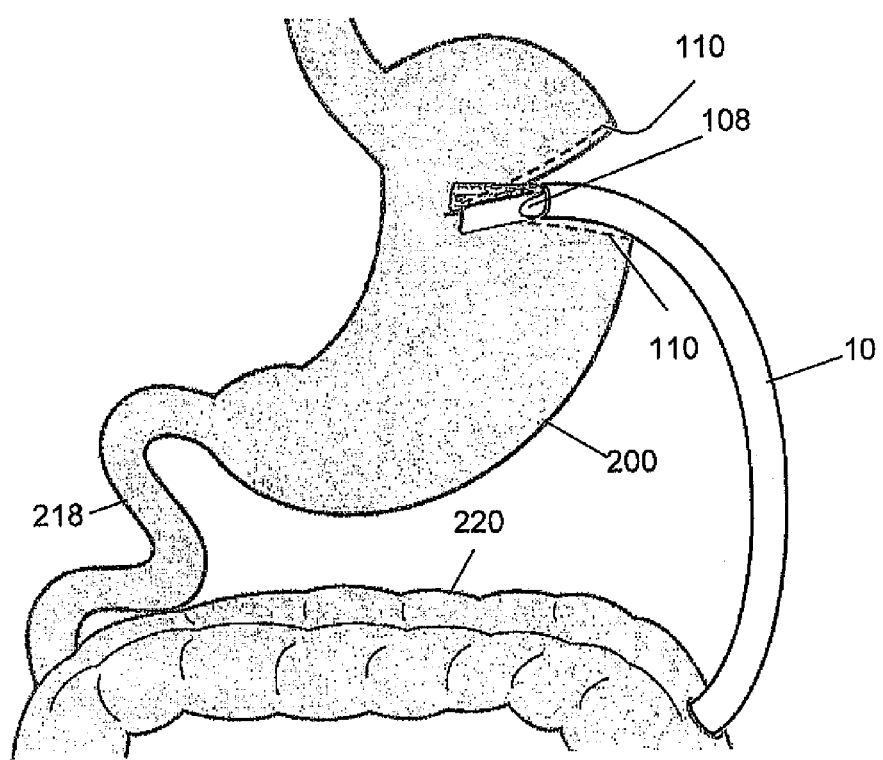
Figure 21C:
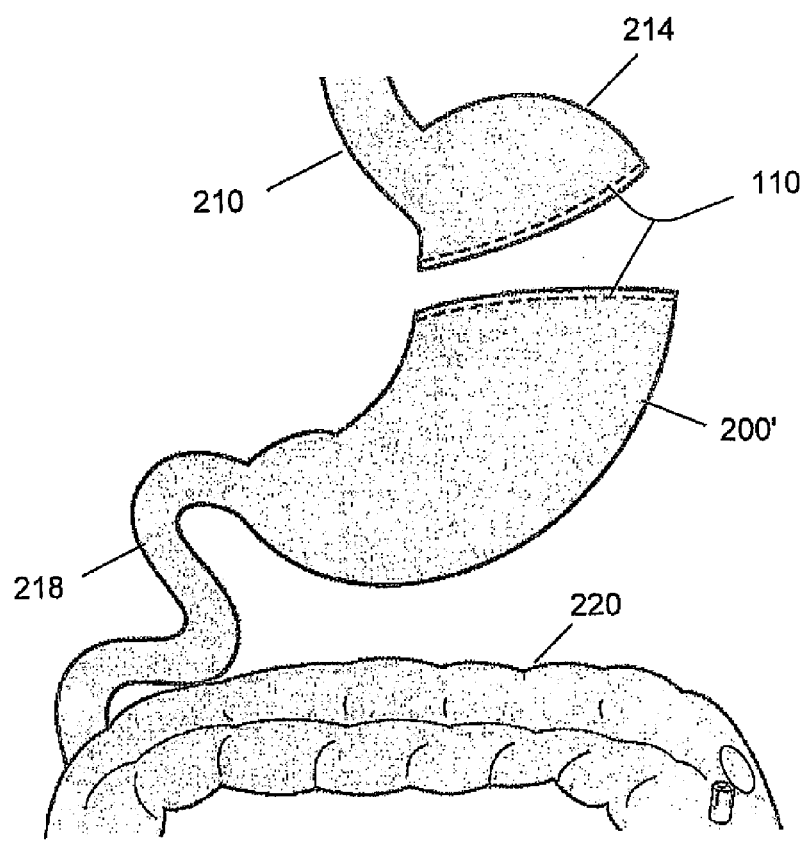

FIGS. 21A to 21C illustrate a second way of endoscopically performing a mini Roux-en-Y Gastric Bypass. Instead of starting the procedure by introducing the endoscope transorally, an endoscope is introduced through the anus into the colon. A hole is made in the wall of colon 220 and an endoscopic device 10 comprising linear stapler 108 is pushed out through the hole and advanced until it is facing the stomach (FIG. 21A). The stomach is bisected as described with respect to embodiment 1 (FIG. 21B). After the stomach is completely bisected to separate pouch 214 from the remainder of the stomach 200', the endoscope with the linear stapler is withdrawn (FIG. 21C). The procedure is completed by introducing a working channel endoscope through the hole in the colon to bring a loop of intestine 218 (transected as a Roux limb or not transected as in a mini gastric bypass) to the pouch. In this trans colon approach the operating tools are already in the abdominal cavity, therefore the entire procedure can be completed without entering the esophagus and making a hole in the stomach. After connecting the loop to the bowel an endoscope with stapler on the distal end is introduced to the colon and used to seal the hole.

Roux-En-Y Gastric Bypass

Embodiment 3

FIGS. 22A to 22G schematically illustrate the steps of another method of performing a mini Roux-en-Y Gastric Bypass. In embodiment 1, described hereinabove, the articulation section of the endoscope must be bent through approximately 180 degrees in the abdominal cavity in order to bring the stapler into the correct orientation to begin bisection of the stomach. The present embodiment eliminates the necessity of transgastric articulation of the endoscope.

Figure 22C:
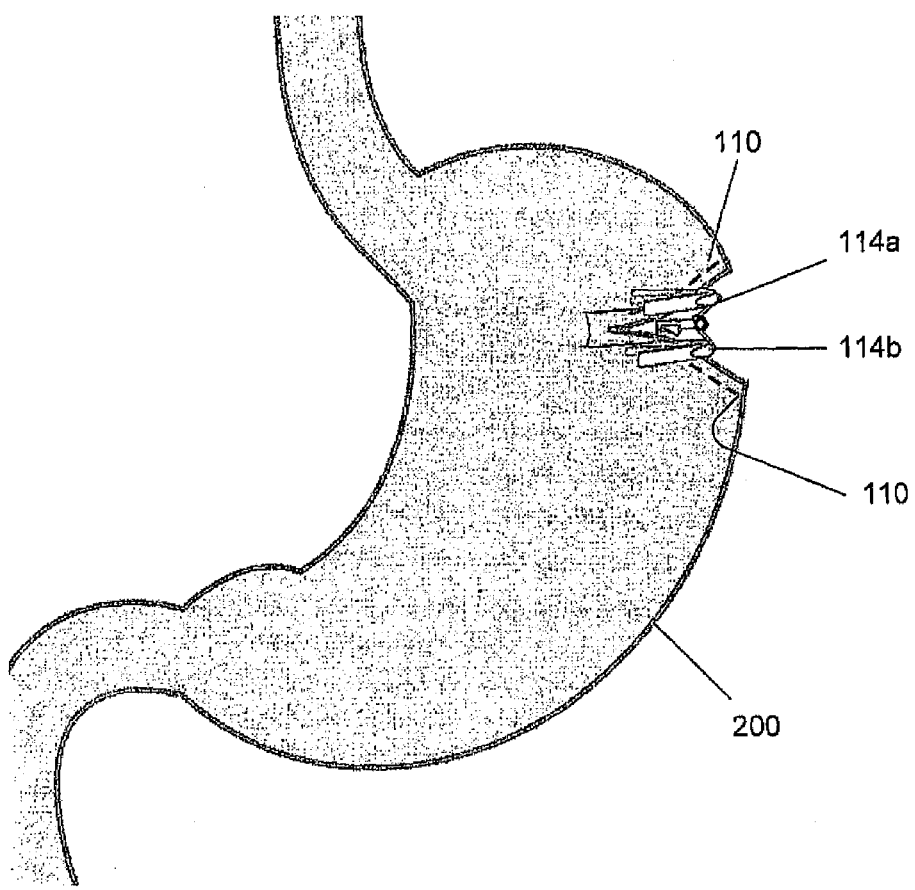

The endoscope is introduced through esophagus 210 into stomach 200. A hole is made in the stomach wall with a surgical cutting tool introduced through a working channel. After the hole has been made, the distal end of endoscope 10, which has two linear staplers 114a and 114b attached to it, is pushed through the hole to the outside of the stomach (FIG. 22A). The jaws of the staplers, which were held in the closed configuration while the endoscope was moved to the operating site, are then spread apart (FIG. 22B). The endoscope is then pulled in the proximal direction, the tissue of the stomach on either side of the hole slides between the open jaws of the staplers, the jaws are closed, and the staples are fired. Each of the staplers 114a and 114b fires an array that produces a single staple line 110. It should be noted that embodiments of linear staplers that apply a double or triple staple line may also be utilized if the surgeon prefers such an approach, as some surgeons currently do in some laparoscopic or open gastric bypass cases. Finally a knife attached to one of the staples is used to slice the tissue between the staple lines (FIG. 22C).

Figure 22D:
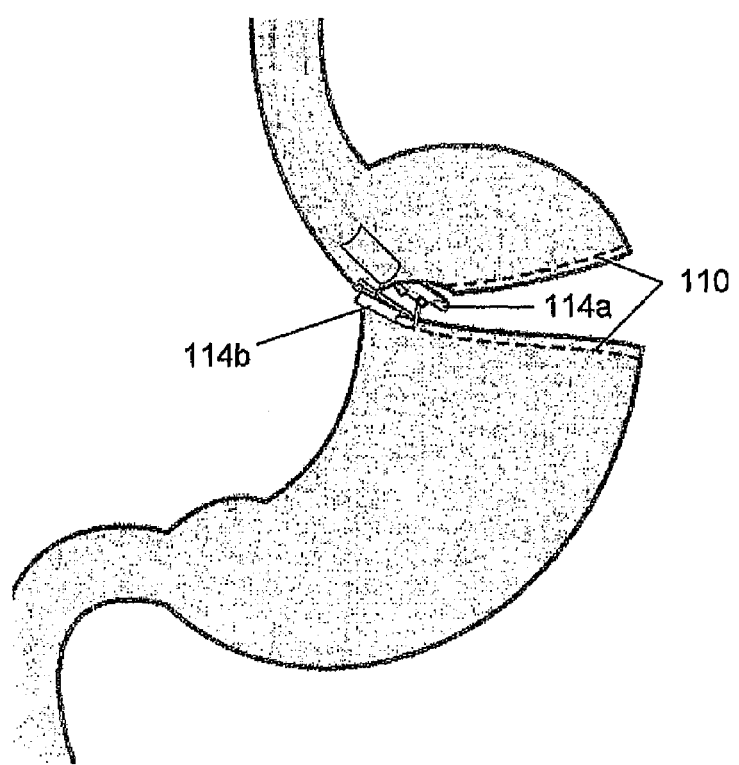
Figure 22E:
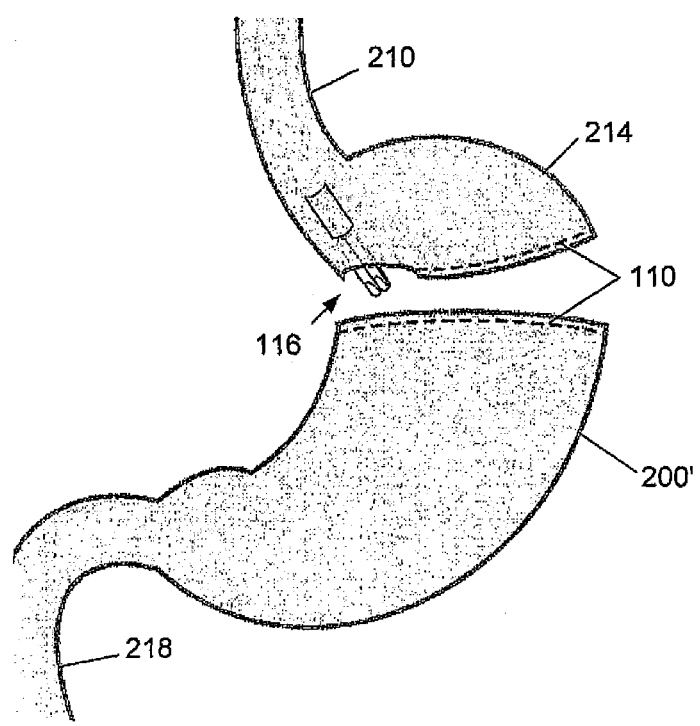
Figure 22F:
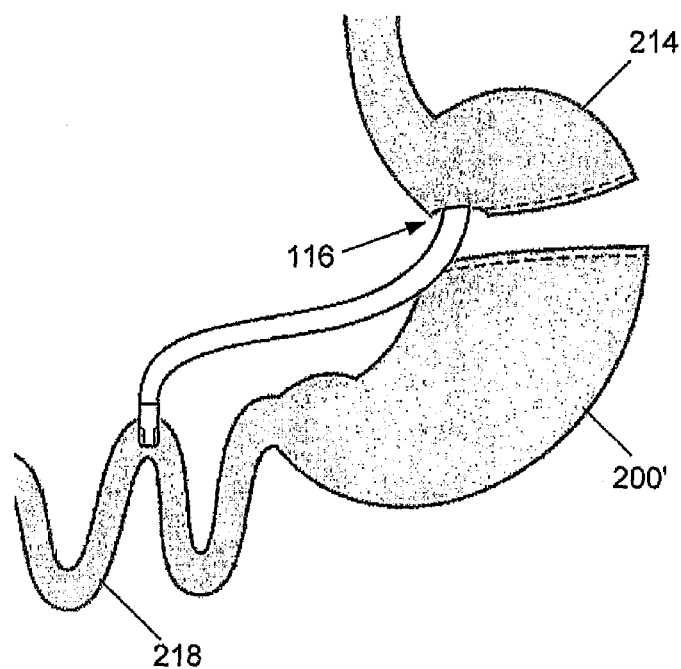

The jaws of the staplers are then opened, the endoscope moved proximally and another "bite" is taken increasing the length of staple lines 110. When it is time to perform the last "bite", which will bisect the stomach, stapler 144a is not activated (FIG. 22D). The result is that the stomach is bisected into two parts, the larger lower part 200', whose upper edges are entirely closed by staple line 110 and an upper pouch 214, which has a hole 116 in it (FIG. 22E).

Figure 22G:
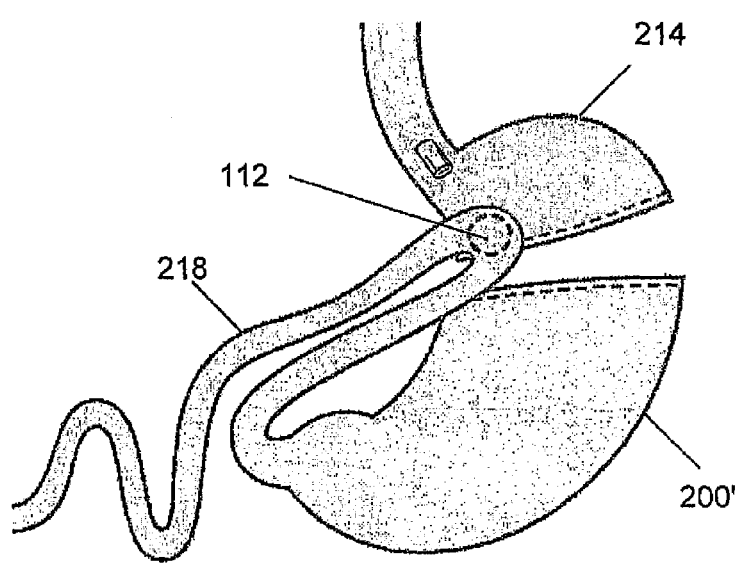

After completing the bisection of the stomach the stapler endoscope is withdrawn and a working channel endoscope introduced. The working channel is pushed through hole 116 in pouch 214 and maneuvered until the intestine 218 can be grabbed (21F). Finally the endoscope and grabbed intestine are pulled back to the hole where the intestine 218 is attached to pouch 214 by conventional means, e.g. anastomosis button 112 to complete a mini gastric bypass procedure (FIG. 22G). As in the previous embodiments, starting from the stage shown in FIG. 22e, the surgeon can choose any minimally invasive approach that he wishes to cut the small intestine and connect a Roux limb in order to complete a Roux-en-Y procedure.

Although embodiments of the invention have been described by way of illustration, it will be understood that the invention may be carried out with many variations, modifications, and adaptations, without exceeding the scope of the claims.

The invention claimed is:

1. A surgical method comprising positioning an adjustable gastric band having two ends that can be joined around a portion of a stomach, wherein said surgical method is carried out using endoscopic devices introduced through natural body openings without creating any incisions in the abdominal wall for the introduction of said endoscopic devices,
   wherein the adjustable gastric band is applied around the portion of the stomach using a transgastric procedure carried out by introducing the adjustable gastric band and all surgical tools endoluminally,
   wherein said surgical method comprises steps of
      introducing the gastric band and an endoscopic device into the stomach without creating an incision in the abdominal wall,
      using said endoscopic device to cut a hole in a wall of said stomach,
      withdrawing said endoscopic device from said stomach, and
      introducing into said stomach a second endoscopic device having a stapler mounted on a tip of said second endoscopic device, and using said stapler to close said hole.

2. A surgical method for performing a first stage of a Gastric Bypass procedure said surgical method comprising: bisecting a stomach to form a closed pouch, said surgical method carried out
   using endoscopic devices introduced through natural body openings without creating any incisions in the abdominal wall for the introduction of said endoscopic devices,
   wherein, one of said endoscopic devices comprises at least one working channel and a distal end,
   said one of said endoscopic devices also comprises on said distal end at least one linear stapler that applies two parallel lines of staples and a video camera,
   said video camera adapted and oriented to provide a visual representation of an anatomical structure and any surgical or diagnostic tools present in a field of view of said video camera.

3. A surgical method according to claim 2, wherein the endoscopic devices are introduced transorally through the esophagus into the stomach.

4. A surgical method according to claim 2, wherein the endoscopic devices are introduced through the anus and part of the colon into the abdominal cavity.

5. A surgical method according to claim 2 further comprising the step of performing a second stage of the Gastric Bypass procedure.

6. A surgical method according to claim 5, wherein the Gastric Bypass procedure is a mini Gastric Bypass.

7. A surgical method according to claim 5, wherein the Gastric Bypass procedure is a complete Roux-en-Y Gastric Bypass.

8. A surgical method comprising positioning an adjustable gastric band having two ends that can be joined around a portion of a stomach, wherein said surgical method is carried out using endoscopic devices introduced through natural body openings without creating any incisions in the abdominal wall for the introduction of said endoscopic devices,
   wherein the stomach wall is plicated, forming plications, and attached to an external wall of a cardia in at least two spaced apart locations using a GERD endoscope,
   wherein a working channel endoscope with the adjustable gastric band held in front of the working channel endoscope by a grasping tool is introduced through the esophagus into the stomach,
   wherein the adjustable gastric band is implanted using the grasping tool.

9. A surgical method according to claim 8, wherein the adjustable gastric band is applied within said stomach around loops created by said plications.

10. A surgical method according to claim 8, wherein the adjustable gastric band is applied around said external wall of the cardia within loops created by said plications.

* * * * *